(12) United States Patent
White et al.

(10) Patent No.: US 8,512,406 B2
(45) Date of Patent: Aug. 20, 2013

(54) VERTEBRAL BODY AND DISC SPACE REPLACEMENT DEVICES

(75) Inventors: John L. White, Bartlett, TN (US);
Steven D. DeRidder, Bartlett, TN (US);
Bret M. Berry, Cordova, TN (US);
George Frey, Englewood, CO (US);
Jeffrey D. Moore, Horn Lake, MS (US);
Jeffrey L. Scifert, Arlington, TN (US);
Troy D. Drewry, Memphis, TN (US);
Jeffrey S. Smithey, Collierville, TN (US); Eric C. Lange, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 744 days.

(21) Appl. No.: 12/584,392

(22) Filed: Sep. 4, 2009

(65) Prior Publication Data
US 2010/0004752 A1   Jan. 7, 2010

Related U.S. Application Data

(63) Continuation of application No. 11/333,167, filed on Jan. 17, 2006, now Pat. No. 7,615,078, which is a continuation of application No. 10/394,988, filed on Mar. 21, 2003, now Pat. No. 6,991,653, which is a continuation-in-part of application No. 10/103,237, filed on Mar. 21, 2002, now Pat. No. 6,758,862.

(51) Int. Cl.
*A61F 2/44* (2006.01)
(52) U.S. Cl.
USPC ........................................ 623/17.16

(58) Field of Classification Search
USPC .................. 623/17.11–17.16; 446/117, 128, 446/476
See application file for complete search history.

(56) References Cited

U.S. PATENT DOCUMENTS

| | | | |
|---|---|---|---|
| 2,677,369 A | 5/1954 | Knowles | |
| 4,309,777 A | 1/1982 | Patil | |
| 4,599,086 A | 7/1986 | Doty | |
| 4,820,305 A | 4/1989 | Harms et al. | |
| 4,834,757 A | 5/1989 | Brantigan | |
| 4,938,768 A * | 7/1990 | Wu ............................ | 623/23.47 |
| 5,062,850 A | 11/1991 | MacMillan et al. | |
| 5,147,404 A | 9/1992 | Downey | |
| 5,192,327 A | 3/1993 | Brantigan | |
| 5,443,515 A | 8/1995 | Cohen et al. | |
| 5,458,638 A | 10/1995 | Kuslich et al. | |
| 5,458,641 A | 10/1995 | Ramirez Jimenez | |
| 5,534,029 A | 7/1996 | Shima | |
| 5,571,190 A | 11/1996 | Ulrich et al. | |
| 5,609,635 A | 3/1997 | Michelson | |
| 5,609,637 A | 3/1997 | Biedermann et al. | |
| 5,702,451 A | 12/1997 | Biedermann et al. | |

(Continued)

FOREIGN PATENT DOCUMENTS

| | | |
|---|---|---|
| DE | 19738052 A1 | 3/1999 |
| EP | 1346709 A | 9/2003 |

(Continued)

*Primary Examiner* — Kevin T Truong
*Assistant Examiner* — Diana S Jones

(57) ABSTRACT

A vertebral replacement device for supporting adjacent vertebrae includes a vertebral body member having at least one of an upper or lower disc replacement member engaged thereto at one end thereof. The disc replacement device can be positioned in a spinal disc space when disengaged from the vertebral body member.

7 Claims, 21 Drawing Sheets

(56) References Cited

U.S. PATENT DOCUMENTS

| | | | |
|---|---|---|---|
| 5,702,455 | A | 12/1997 | Saggar |
| 5,776,199 | A | 7/1998 | Michelson |
| 5,782,832 | A | 7/1998 | Larsen et al. |
| 5,861,041 | A | 1/1999 | Tienboon |
| 5,865,845 | A | 2/1999 | Thalgott |
| 5,897,556 | A | 4/1999 | Drewry et al. |
| 5,972,031 | A | 10/1999 | Biedermann et al. |
| 5,975,933 | A | 11/1999 | Yamaguchi et al. |
| 5,989,290 | A * | 11/1999 | Biedermann et al. ...... 623/17.11 |
| 6,086,613 | A | 7/2000 | Camino et al. |
| 6,102,949 | A | 8/2000 | Biedermann et al. |
| 6,106,557 | A * | 8/2000 | Robioneck et al. ........ 623/17.15 |
| 6,159,211 | A | 12/2000 | Boriani et al. |
| 6,193,756 | B1 * | 2/2001 | Studer et al. ............... 623/17.15 |
| 6,200,348 | B1 | 3/2001 | Biedermann et al. |
| 6,241,771 | B1 | 6/2001 | Gresser et al. |
| 6,245,108 | B1 | 6/2001 | Biscup |
| 6,296,665 | B1 | 10/2001 | Strnad et al. |
| 6,454,806 | B1 | 9/2002 | Cohen et al. |
| 6,468,311 | B2 | 10/2002 | Boyd et al. |
| 6,585,770 | B1 | 7/2003 | White et al. |
| 6,758,862 | B2 | 7/2004 | Berry et al. |
| 6,776,800 | B2 | 8/2004 | Boyer, II et al. |
| 6,796,723 | B2 | 9/2004 | Kim et al. |
| 6,808,538 | B2 | 10/2004 | Paponneau |
| 2003/0009235 | A1 | 1/2003 | Manrique et al. |
| 2003/0125739 | A1 | 7/2003 | Bagga et al. |
| 2003/0191531 | A1 | 10/2003 | Berry et al. |
| 2006/0116770 | A1 | 6/2006 | White et al. |

FOREIGN PATENT DOCUMENTS

| | | |
|---|---|---|
| JP | 04-179077 | 6/1992 |
| JP | 10-41023 | 2/1998 |
| WO | WO 03/053290 A1 | 7/2003 |

* cited by examiner

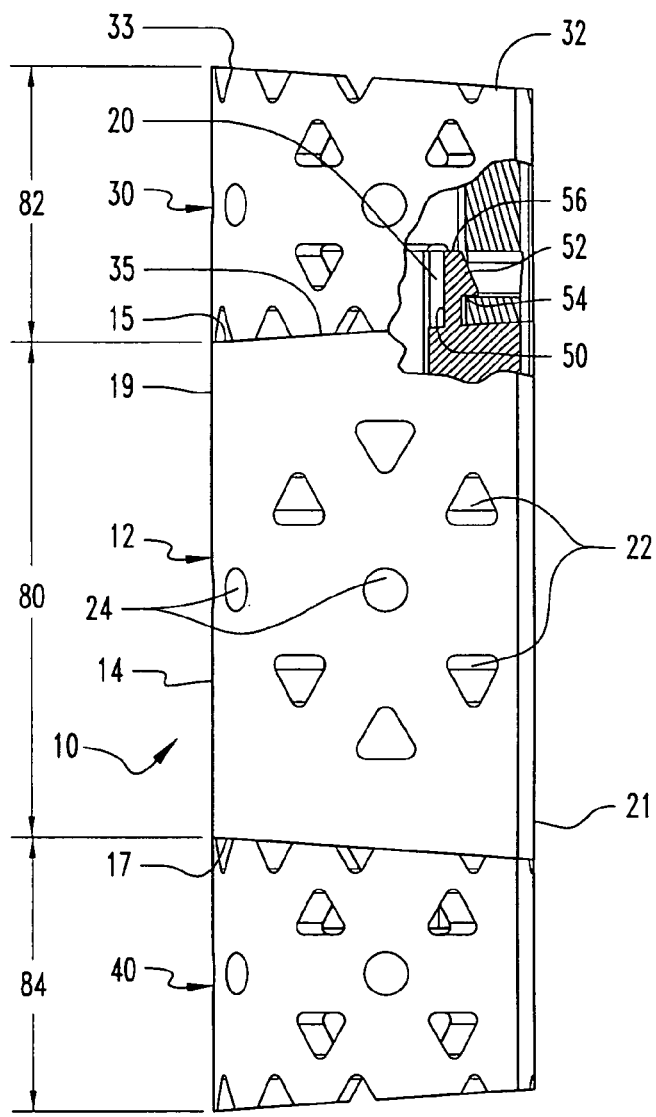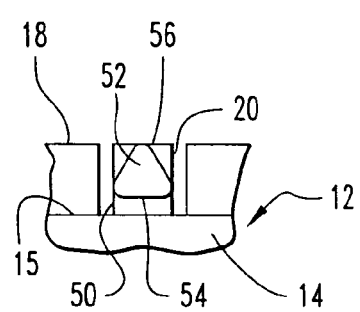
Fig. 4
Fig. 3

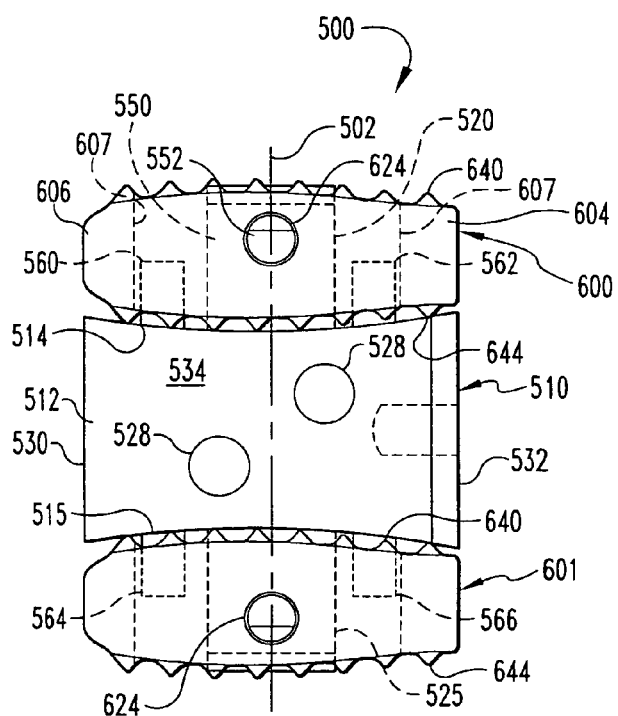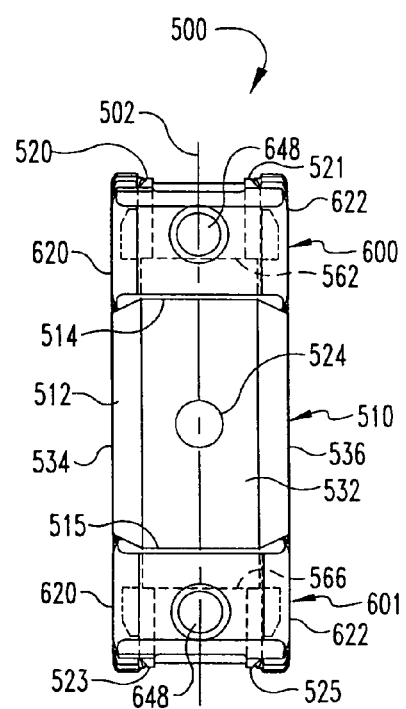
Fig. 22  Fig. 23

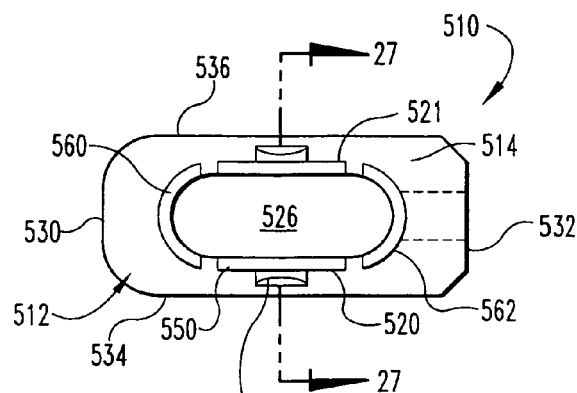
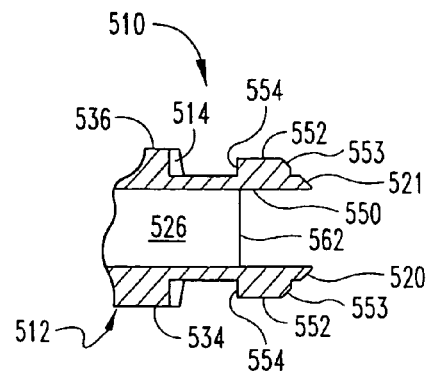
Fig. 26          Fig. 27
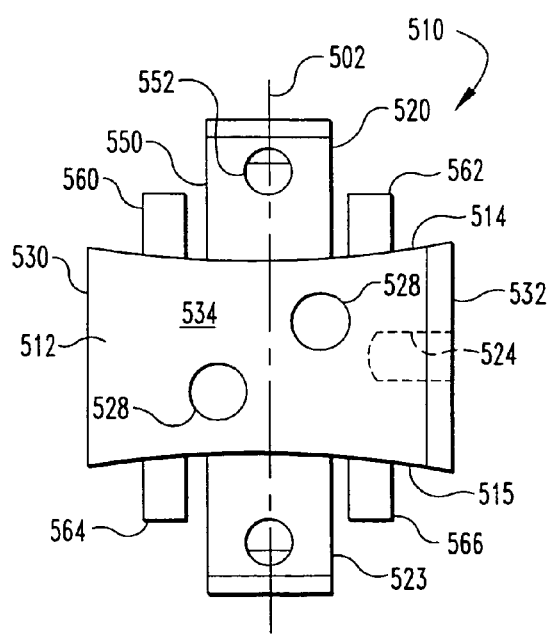
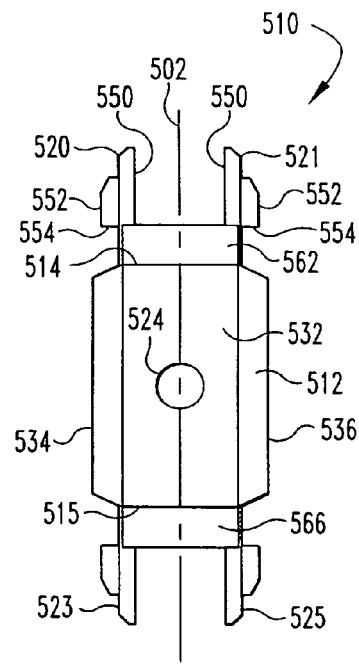
Fig. 24          Fig. 25

VERTEBRAL BODY AND DISC SPACE REPLACEMENT DEVICES

CROSS-REFERENCE TO RELATED APPLICATIONS

This application is a continuation application of U.S. patent application Ser. No. 11/333,167 filed on Jan. 17, 2006 now U.S. Pat. No. 7,615,078, which is a continuation application of U.S. patent application Ser. No. 10/394,988, filed on Mar. 21, 2003 and issued as U.S. Pat. No. 6,991,653 on Jan. 31, 2006, which is a continuation-in-part application of U.S. patent application Ser. No. 10/103,237 filed on Mar. 21, 2002, and issued as U.S. Pat. No. 6,758,862 on Jul. 6, 2004. Each of these referenced applications is incorporated herein by reference in its entirety.

BACKGROUND

The present invention is directed to devices for replacement of one or more vertebral bodies and/or one or more disc spaces between vertebrae of a spinal column.

The repair and reconstruction of bony structures is sometimes accomplished by directly fixing adjacent bony structures to each other, such as by a plate. In other instances, bone growth inducing material can be introduced between the adjacent bony structures, which over time results in a solid bony connection. In some instances, the adjacent bony structures are not sufficiently strong to maintain their patency as the bone heals or the bone grows between the adjacent structures through the bone growth inducing material. In these instances, mesh structures or cages have been provided to engage the adjacent bony structures to provide additional stability. The cages are generally hollow and can be configured to contact the harder cortical bone of the adjacent bony structures. The hollow portion of the cages can be filled with bone growth inducing material.

Devices have also been provided to replace a removed vertebral body and to provide a support structure between the remaining vertebrae on either side of the one or more removed vertebral bodies. One example of such a device is provided in U.S. Pat. No. 5,192,327.

The '327 patent describes oval or hemi-oval rings which can be used in isolation in a disc space or stacked one upon another in interdigitating fashion for replacement of a vertebral body. The rings have ridges along their top and bottom faces that form peaks and valleys to allow the stacked rings to interdigitate when stacked. One problem with these interdigitating ridges is that the stack of rings can slide relative to one another in the direction of the ridges when stacked. The '327 patent also discloses a connecting bar extending through the stacked rings transversely to the ridges to prevent relative sliding between the stacked rings. In order to use the connecting bar in surgery, the surgeon must be provided with a multitude of bars of differing heights and/or "custom fit" the bar as needed for the height of the particular set of stacked cages. In addition, the stacked cages can separate longitudinally even when the connecting bar extends through the stacked cages.

There remains a need for improved devices for replacing one or more vertebral bodies and/or one or more disc spaces in a spinal column. The present invention is directed to satisfying these needs, among others.

DESCRIPTION OF THE FIGURES

FIG. 3 is a side elevation view of the vertebral replacement device of FIG. 1 in partial section to illustrate the interconnection between disc replacement members and a vertebral body member of the device.

FIG. 4 is an elevational view of an engaging member comprising a portion of the vertebral body member of the device of FIG. 1.

FIG. 22 is an elevation view of a vertebral replacement device according to another embodiment of the present invention.

FIG. 23 is an end elevation view of the vertebral replacement device of FIG. 22.

FIG. 24 is an elevation view of a vertebral body member comprising a portion of the vertebral replacement device of FIG. 22.

FIG. 25 is an end elevation view of the vertebral body member of FIG. 24.

FIG. 26 is a plan view of the vertebral body member of FIG. 24.

FIG. 27 is a section view of a portion of the vertebral body member of FIG. 24 through line 27-27 of FIG. 26.

DESCRIPTION OF THE ILLUSTRATED EMBODIMENTS

Figure 1:
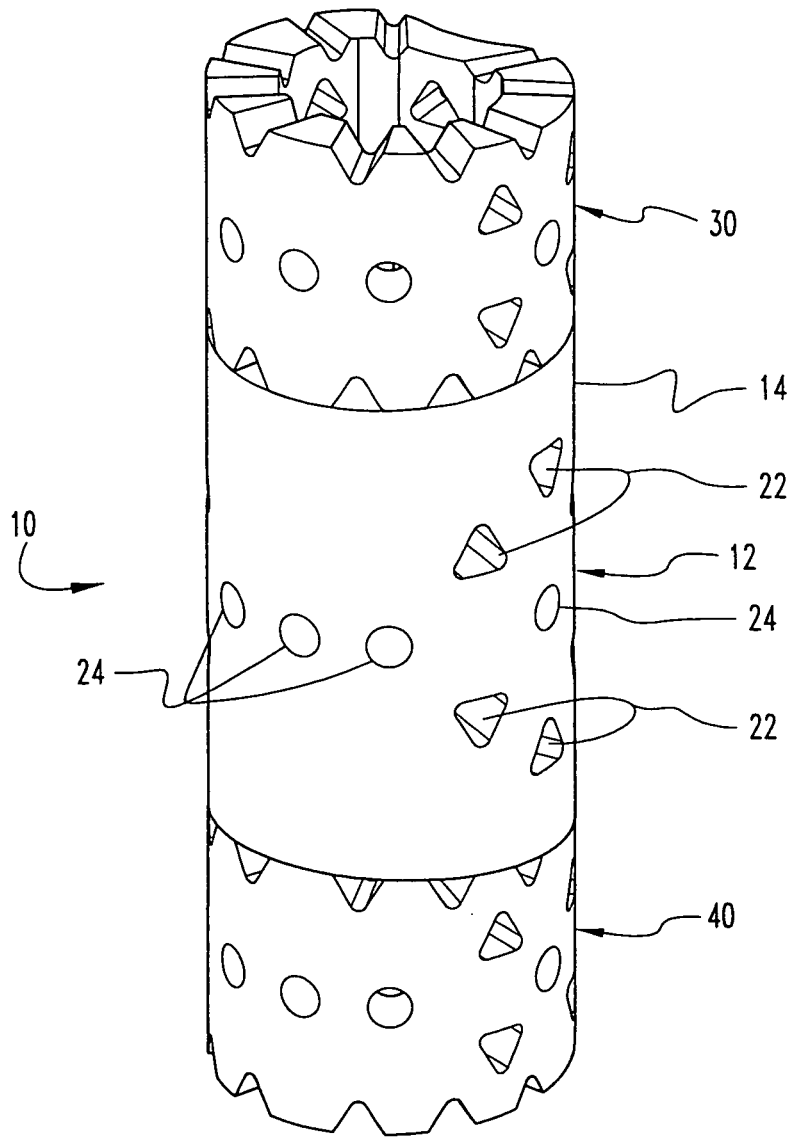
FIG. 1 is a perspective view of a vertebral replacement device according to one embodiment of the present invention.

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

The present invention relates to devices for replacing one or more vertebral bodies in the spinal column and/or one or more disc spaces between adjacent vertebrae. It is contemplated that the replacement devices will support adjacent ones of the intact vertebrae during fusion thereof. It is further contemplated that one or more components of the vertebral replacement devices can be positioned in a disc space between adjacent vertebrae for supporting the adjacent vertebrae during fusion thereof. Application in non-fusion procedures is also contemplated In one embodiment, the device can employ current mesh or cage-type devices for engagement with adjacent bony structures, although other types of bone supporting devices are also contemplated. The vertebral replacement device can have a tubular form with a hollow chamber extending therethrough. The adjacent vertebrae are supported by opposite ends of the device and the chamber can be filled with bone growth inducing or osteogenetic material. The ends of the device include flattened plateau-like end surfaces that can be formed at the junction between bars defining the mesh wall structure of the device.

In one embodiment, the vertebral replacement device includes a connecting member and an upper member attached to an upper end of the connecting member and a lower member attached to a lower end of the connecting member. Each of the members can have a generally kidney bean cross-sectional shape in the plane transverse to the central axis of the assembled device. Other cross-sectional shapes are also contemplated, including circular, racetrack-shaped, rectangular, square, oval, D-shaped, triangular, boomerang, banana, or other polygonal shape. Each of the upper and lower members can include an interior chamber. The connecting member can also include an interior chamber that generally aligns with the interior chambers of the upper and lower members engaged thereto.

In one embodiment, the upper and lower members can be fabricated from a tubular mesh having apertures through its wall. One example of a tubular mesh is provided in U.S. Pat. No. 5,897,556, which is incorporated herein by reference in its entirety. The connecting member can also be fabricated from a tubular mesh. Further forms contemplate that the upper and lower members and connecting member can be a tubular body with solid walls or wall structure including one or more openings.

In one embodiment, the upper and lower members can be telescopically and non-rotatably engaged with the connecting member. The connecting member includes an upper extension and a lower extension extending therefrom. The upper and lower extensions are in the form of substantially continuous rings extending around the respective ends of the vertebral body or connecting member. Other forms for the upper and lower extensions are also contemplated. The upper and lower extensions are received in the interior chamber of the respective upper or lower members when the upper and lower members are engaged to the connecting member. In another embodiment, extensions are provided on the upper and lower members, and these extensions are received in an interior chamber or opening at respective ends of the connecting member.

Each of the upper and lower extensions, and each of the chambers of the upper and lower members, can have a non-circular cross-section and interface to prevent relative rotation between the connecting member and the upper or lower member engaged thereto.

In one embodiment, the upper and lower extensions of the connecting member each include an engaging member which can be flexed inwardly as the respective upper or lower member is placed around the respective extension of the connecting member. The engaging member fits into an opening or aperture in the inner wall surface of the respective upper and lower members to axially secure the respective upper and lower members to the connecting member.

Any one or all of the components of the vertebral replacement devices can be made from any biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well.

Any suitable osteogenetic material or composition is contemplated for placement within the chambers defined by the components or the vertebral replacement device. Such osteogenic material includes, for example, autograft, allograft, xenograft, demineralized bone, synthetic and natural bone graft substitutes, such as bioceramics and polymers, and osteoinductive factors. Where bony material is placed within the chambers of the components of the vertebral replacement device, the material can be pre-packed into the hollow chambers before the device is implanted, or can be pushed through the plurality of wall openings after the device is in position in the spinal column. A separate carrier to hold the materials within the chambers of the device can also be used. These carriers can include collagen-based carriers, bioceramic materials, such as BIOGLASS®, hydroxyapatite and calcium phosphate compositions. The carrier material can be provided in the form of a sponge, a block, folded sheet, putty, paste, graft material or other suitable form. Moreover, the osteogenetic compositions contained within the vertebral replacement device can comprise an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agent, held within a suitable carrier material.

Figure 2:
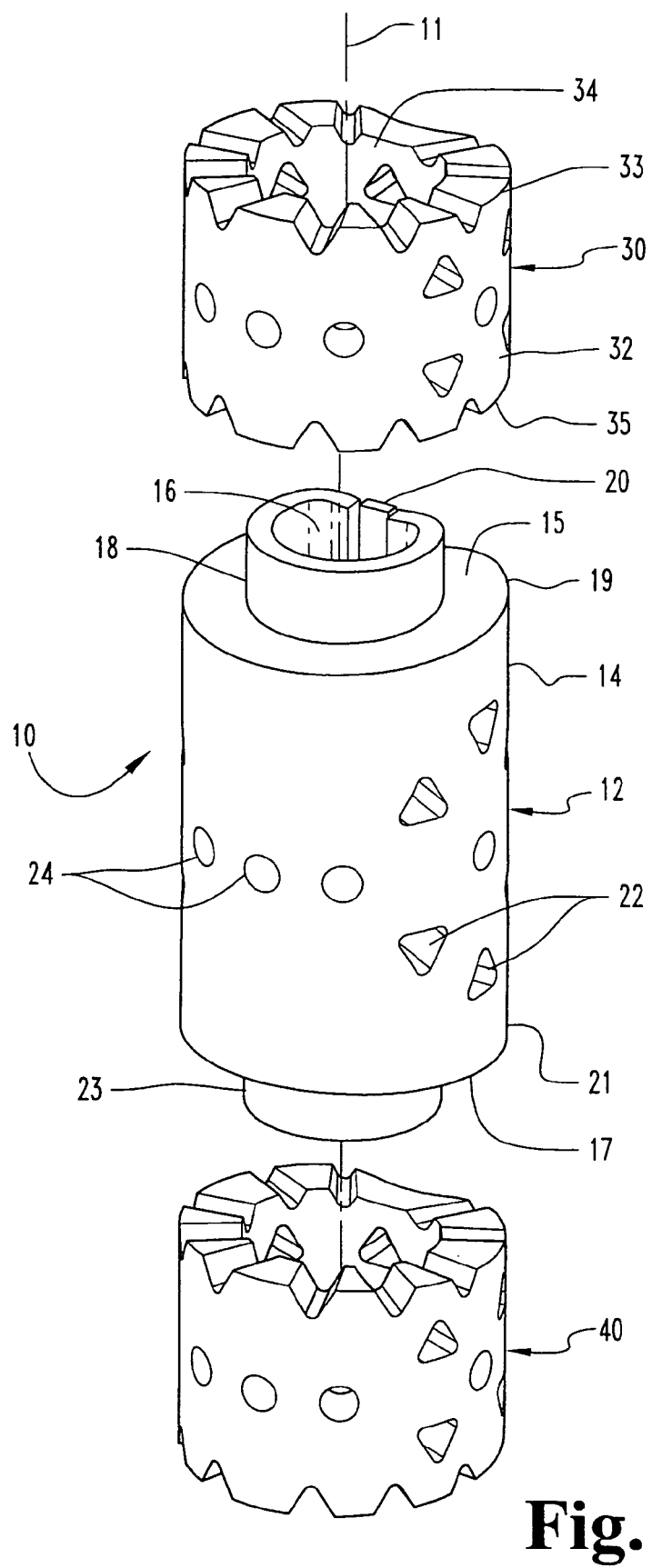
FIG. 2 is an exploded perspective view of the vertebral replacement device of FIG. 1.

In FIGS. 1-2, a vertebral replacement device 10 includes a connecting member 12, an upper member 30, and a lower member 40. Device 10 is illustrated as having a tubular form that extends along a longitudinal axis 11 and defines a chamber extending therethrough along axis 11. Bone growth can occur through this chamber for fusion between the vertebral bodies supported at each end of device 10.

Connecting member 12 includes a body 14 extending between an upper end 19 and an opposite lower end 21. Connecting member 12 further includes an upper extension 18 and a lower extension 23. Connecting member 12 has an inner wall surface 13 (FIG. 5) that defines a chamber 16 extending between and opening at the outer ends of the extensions 18, 23. Each of the extensions 18, 23 extends outwardly from the respective end 19, 21 of body 14 and around chamber 16. End surface 15 extends around upper extension 18, and end surface 17 extends around lower extension 23. In the illustrated embodiment, extensions 18, 23 are substantially continuous rings extending from their respective end 19, 21. Other embodiments contemplate other forms for the extensions, such as, for example, a series of two or more flexible engaging members (such as engaging member 20 discussed below) or rigid engaging members.

The wall of body 14 includes a number of triangular apertures 22 which extend through the wall and communicate with chamber 16. Other shapes for apertures 22 are also contemplated, including non-circular shapes such as a square, diamond, oval and/or rectangular shapes, circular shapes, and/or polygonal shapes. The wall of body 14 also includes a number of holes 24 extending at least partially therethrough. Holes 24 can be threaded or otherwise sized and/or configured for engagement with one or more insertion instruments (not shown.)

Figure 5:
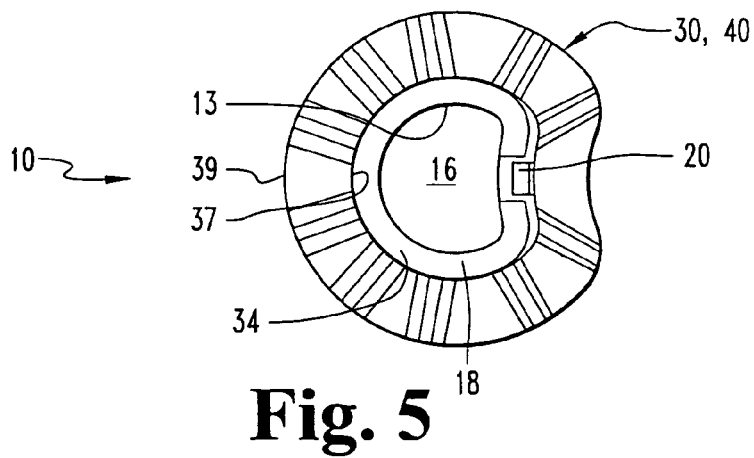
FIG. 5 is an end view of the vertebral replacement device of FIG. 1.

Referring further to FIGS. 3-5, the substantially continuous wall of each of the extensions 18, 21 is interrupted by an engaging member 20. Only engaging member 20 for upper extension 18 is illustrated, it being understood that lower extension 23 can also be provided with an identical or similar engaging member. Engaging members 20 secure upper member 30 and lower member 40 to respective ends of connecting member 12, resisting axial dislocation of upper member 30 and lower member 40 away from connecting member 12 along axis 11. Engaging members 20 can also resist axial rotation of upper and lower members 30, 40 relative to connecting member 12 about axis 11. Other embodiments contemplate that more than one engaging member 20 is provided in the wall of one or both of the extensions 18, 23. Further embodiments contemplate that wall of one or both of the extensions 18, 23 is not substantially continuous, but rather is continuous or includes a number of discrete wall portions sufficiently spaced and sized about body 14 of connecting member 12 for engagement with upper and lower members 30, 40.

Engaging member 20 includes a projection or engaging portion 52 and a stem 50 connected or integrally formed with end surface 15 of body 14. Stem 50 has a reduced thickness to allow engaging member 20 to deflect inwardly in response to a force applied to engaging portion 52. Engaging portion 52 projects outwardly from stem 50 and has a triangular shape tapering from an engaging surface 54 to an upper end 56. Other configurations for engaging member 20 are also contemplated. For example, engaging member 20 can be provided with an engaging portion 52 in the form of a partially spherical or rounded nub, a receptacle, rectangular or polygonal shaped tab or projection. Engaging portion 52 can also correspond to the shape the aperture 22 in which it is received. Engaging member 20 can also be a snap ring, collet, bayonet lock, or surface irregularity that resists axial movement of the engaged upper member 30 and lower member 40 away from connecting member 12 along axis 11.

Figure 6:
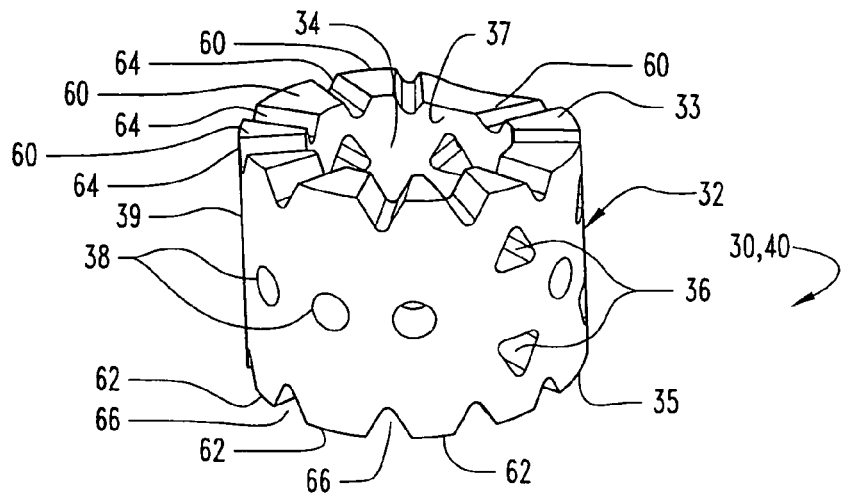
FIG. 6 is a perspective view of a disc replacement member comprising a portion of the vertebral replacement device of FIG. 1.
Figure 7:
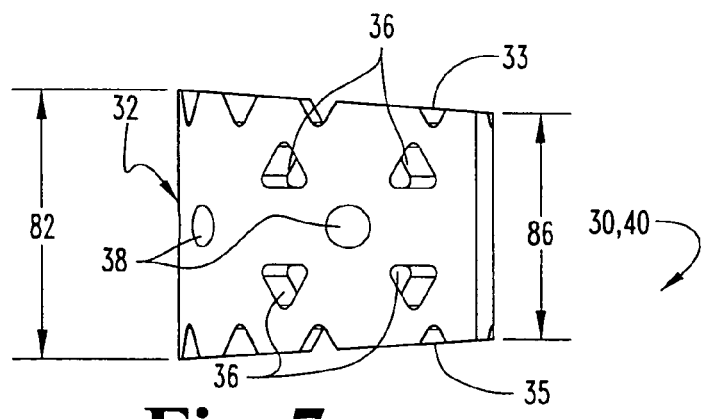
FIG. 7 is an elevation view of the disc replacement device of FIG. 6.

Referring also to FIGS. 6-7, upper and lower members 30, 40 are illustrated as being identical, although it is also contemplated that upper member 30 and lower member 40 can be provided with different configurations and/or sizes. With respect to FIGS. 6 and 7, only upper member 30 will be further described, it being understood that lower member 40 can be provided with identical features.

Upper member 30 includes a body 32 extending between an upper end 33 and a lower end 35. Body 32 has a height 82 between the upper and lower ends 33, 35. Height 82 can be selected so that upper member 30 fits within an intervertebral disc space between adjacent vertebrae. Upper end 33 and lower end 35 can be sloped to converge toward one another and form a height 86 opposite height 82. The sloped ends 33, 35 allow upper member 30 to restore and/or conform to the natural inclination between the adjacent endplates of the vertebral bodies. It is further contemplated that ends 33, 35 can be parallel to one another.

Body 32 has an inner wall surface 37 defining a chamber 34 that extends between and opens at ends 33, 35. As shown in FIG. 5, body 32 has an outer surface 39 that defines a kidney-shaped cross section transverse to longitudinal axis 11. Other cross-sectional shapes are also contemplated, including, for example, circular cross-sections and non-circular cross-sections, such as oval, triangular, square, rectangular, polygonal, boomerang shaped, D-shaped, or racetrack shaped cross-sections. In the illustrated embodiment, connecting member 12 has the same cross-sectional shape as the upper and lower members 30, 40 to provide a vertebral replacement body device of uniform cross-sectional shape and size along its height.

Body 32 defines a number of triangular apertures 36 extending at least partially therethrough in communication with chamber 34, and a number of circular holes 38 extending at least partially therethrough from the exterior surface of body 32. Holes 38 or the other holes can be threaded or otherwise sized and/or configured for engagement with one or more insertion instruments.

Body 32 further includes a number of bearing surfaces 60 spaced around first end 32 and bearing surfaces 62 spaced around second end 35. Adjacent ones of each of the bearing surfaces 60 are separated from one another by V-shaped recesses 64. Adjacent ones of each of the bearing surfaces 62 are separated from one another by V-shaped recesses 66. Bearing surfaces 60, 62 are planar and provide a number of plateau-like, generally flat bearing surfaces spaced about the respective end of body 32. Bearing surfaces 60, 62 have a trapezoidal shape in the illustrated embodiment, although other shapes are also contemplated. In the illustrated embodiment, ten such bearing surfaces 60, 62 are provided at each end of body 32. It is also contemplated that fewer than ten or more than ten bearing surfaces could be provided. It is further contemplated that each end of body 32 could be provided with a single, continuous bearing surface extending around chamber 34.

The plateau-like bearing surfaces 60, 62 provide a surface area about the ends of body 32 for bearing support of the adjacent vertebral endplate and to resist subsidence of body 32 into the vertebrae. The plateau-like bearing surfaces 60, 62 provide surface area contact between the end of body 32 and the adjacent endplate, providing frictional resistance to body 32 sliding or twisting relative to the adjacent vertebral endplate.

Upper member 30 and lower member 40 are connected to respective ends of connecting member 12 to provide vertebral replacement body device 10. Upper member 30 is advanced over upper extension 18 so that upper extension 18 extends into chamber 34. Engaging member 20 flexes inwardly as inner wall surface 37 of body 32 passes along engaging portion 52. Engaging portion 52 is configured to reside within one of the apertures 36 extending into the wall of body 32 from chamber 34. When engaging portion 52 and the respective aperture 36 are aligned, engaging member 20 returns towards its pre-insertion position with engaging portion 52 residing in the respective aperture 36. This engages upper member 30 to connecting member 12, resisting movement of upper member 30 away from connecting member 12 along axis 11. It is further contemplated engaging surface 54 engages the adjacent lower surface of the respective aperture 36 to provide a positive seat between bearing surface 15 of connecting member 12 and bearing surfaces 62 about end 33 of upper member 30. Lower member 40 is secured to lower extension 23 in a similar manner.

Bearing surfaces 62 at lower end 35 of upper member 30 bear against end surface 15 extending about upper extension 18 of connecting member 12. This bearing relationship transmits the spinal column load from upper member 30 to connecting member 12. The bearing surfaces of the lower member 40 similarly bear against end surface 17 extending about lower extension 23 of connecting member 12. The end surfaces 15, 17 at the ends of body 14 and the adjacent bearing surfaces of the upper and lower members 30, 40 do not interdigitate. This bearing relationship eliminates stress concentrations and shifting of the components of device 10 that might result from improperly aligned interdigitating surfaces.

Axial rotation of upper member 30 and lower member 40 relative to connecting member 12 is resisted by the interface between upper and lower extensions 18, 23 and the respective inner wall surface of the upper and lower members 30, 40. In the illustrated embodiment, extensions 18, 23 have a non-circular shape, such as the kidney shape shown in FIG. 5. Similarly, the inner wall surface 37 of upper member 30 and also the inner wall surface of lower member 40 have a non-circular shape sized to receive in form fitting engagement the respective upper or lower extension 18, 23. This non-circular form fitting engagement prevents rotation of upper member 30 and lower member 40 relative to connecting member 12.

Device 10 can be used to replace a vertebra that has been removed from the spinal column segment using known techniques. Device 10 is assembled by securing upper member 30 to one end of connecting member 12 and securing lower member 40 to the other end of connecting member 12. This provides a vertebral replacement device 10 that has an overall height that is equal to the sum of the heights 80 of body 14, height 82 of upper member 30, and height 84 of lower member 40 (FIG. 3.)

Figure 8:
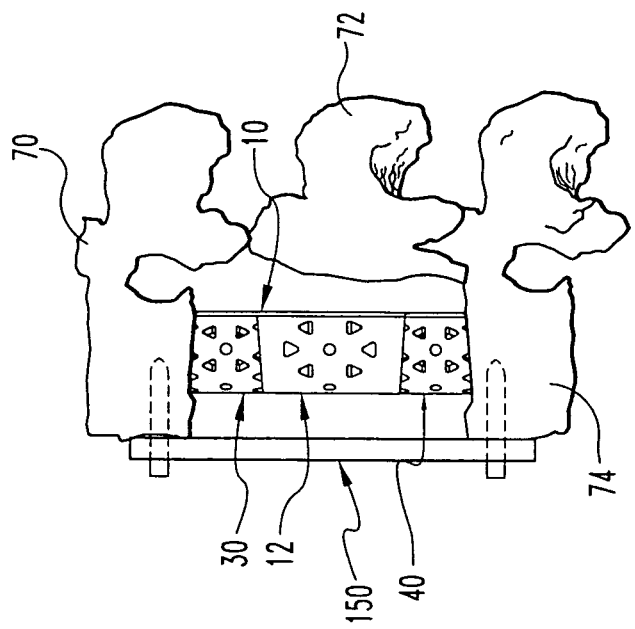
FIG. 8 is an elevational view of the vertebral replacement device of FIG. 1 positioned in the spinal column between two vertebrae.

As shown in FIG. 8, the vertebral replacement device 10 can be placed between vertebra 70 and vertebra 74 after removal of vertebra 72. Replacement of more than one vertebra is also contemplated. Although not required, it is contemplated that height 80 could be representative of that of the removed vertebra and heights 82, 84 could be representative of the heights of the respective disc spaces between the removed vertebra 72 and the remaining vertebrae 70, 74. Also shown in FIG. 8 is a stabilization construct 150 engaged to and extending between vertebrae 70 and 74 to support and stabilize the spinal column segment before, during and, if construct 150 is non-resorbable and left in the patient, after fusion. Stabilization construct 150 can be a rod system, plate system or artificial ligament system. It is further contemplated that stabilization system could be attached to any portion of vertebrae 70 and 74, including the anterior, antero-lateral, lateral, postero-lateral or posterior portions.

It is also contemplated that heights 82 and 84 could be identical or different, and that the ends of upper and lower members 30, 40 could be provided with the same or differing angles of inclination. It is further contemplated that device 10 can comprise a kit having a number of upper members 30 and lower members 40 of various sizes and heights 82, 84. A kit could also include a number of connecting members 12 of various sizes and heights 80. Such a kit would provide the surgeon flexibility in selecting the appropriately size and height for members of a device 10 based on conditions encountered in surgery.

Figure 9:
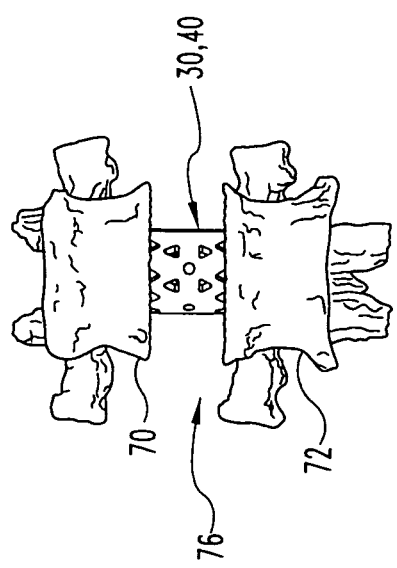
FIG. 9 is an elevational view of one of the disc replacement devices comprising a portion of the vertebral replacement device of FIG. 1 positioned in a spinal disc space between adjacent vertebrae.

FIG. 9 illustrates placement of one of the upper or lower members 30, 40 in disc space 76 between adjacent vertebrae 70, 72 to function as an interbody fusion device. Engagement of stabilization construct to vertebrae 70 and 72 is also contemplated.

It is also contemplated that connecting member 12 could be provided with one end configured to bear against a vertebral endplate, and that only one of the upper and lower members 30, 40 is engaged to the other end of connecting member 12. The assembled device could then be placed between adjacent vertebrae with an end of connecting member 12 and an end of the selected upper or lower member 30, 40 in contact with the adjacent vertebral endplates.

Figure 10:
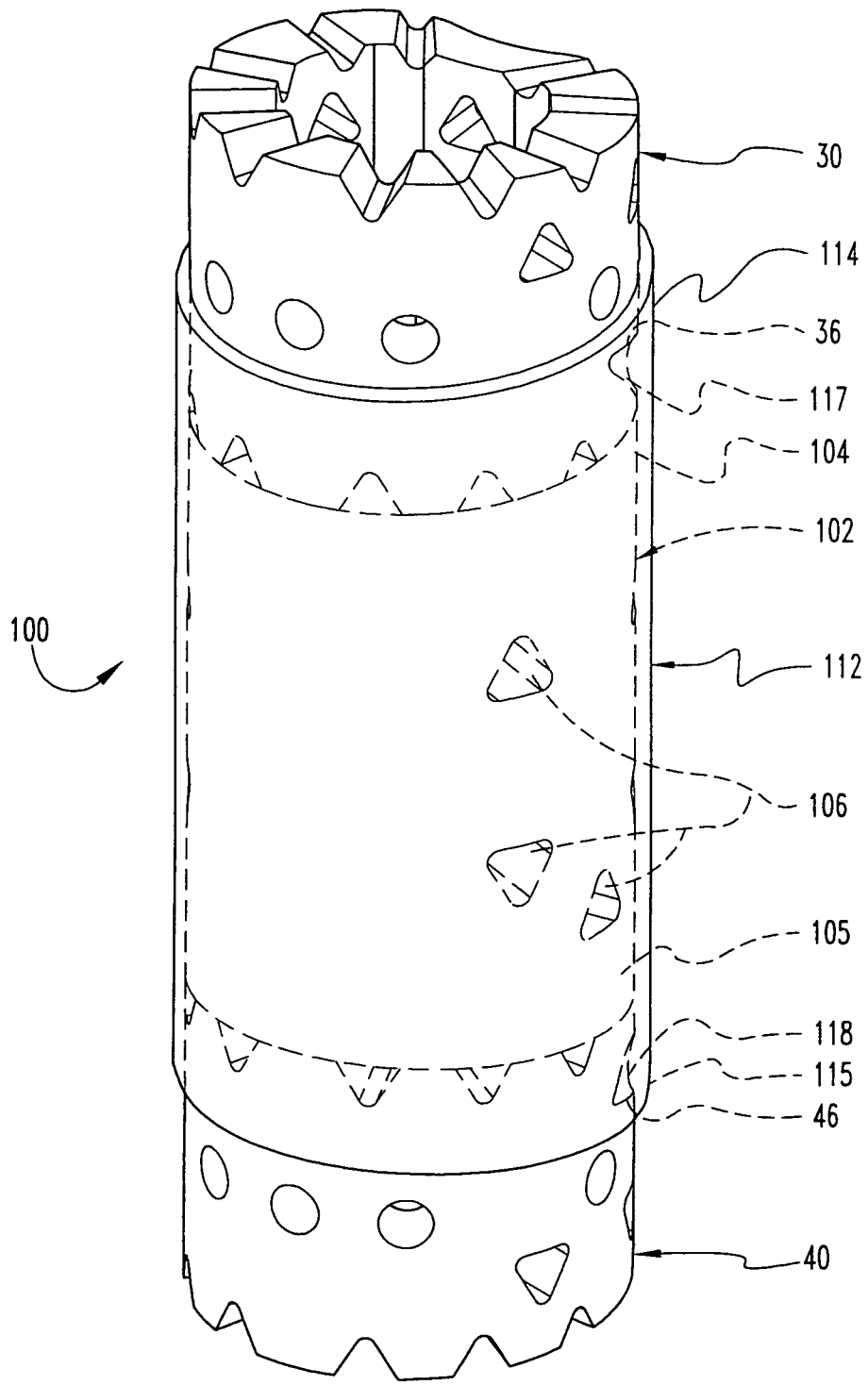
FIG. 10 is a perspective view of another embodiment vertebral replacement device.

In FIG. 10 there is provided an alternate embodiment vertebral replacement device 100. Device 100 includes first disc replacement or upper member 30 and second disc replacement or lower member 40 engaged at opposite ends of a vertebral body or connecting member 102, which can be similar to connecting member 12 discussed above. Connecting member 102 does not include upper and lower extensions extending from end 104 and 105. To secure upper member 30 and lower member 40 to connecting member 102, a sleeve 112 is provided around connecting member 102 that has an upper end 114 overlapping upper member 30 and a lower end 115 overlapping lower member 40.

Sleeve 112 can be provided with engaging members 117, 118 in the form of projections, engaging members, tabs or the like on its inner wall surface. Engaging members 117, 118 engage apertures 36, 46 or other receptacle or detent in the outer wall surfaces of upper member 30 and lower member 40, respectively. Engaging members could also be provided to engage apertures 106 or other receptacle or detent in connecting member 102. So engaged, sleeve 112 resists axial movement of upper member 30 and lower member 40 relative to connecting member 102.

It is further contemplated that rotation of upper member 30 and lower member 40 relative to connecting member 102 could be prevented by a non-circular, telescoping interface between the members such as discussed above. In another embodiment, rotation of upper member 30 and lower member 40 relative to connecting member 102 could be prevented by the engagement of sleeve 112 with the upper and lower members 30, 40 and, if so configured, with connecting member 102. In yet a further form of the embodiment of FIG. 10, the connecting member 102 could be integral with sleeve member 112 to provide upper and lower bearing surfaces within sleeve 112 for support of upper member 30 and lower member 40 thereon.

Figure 11:
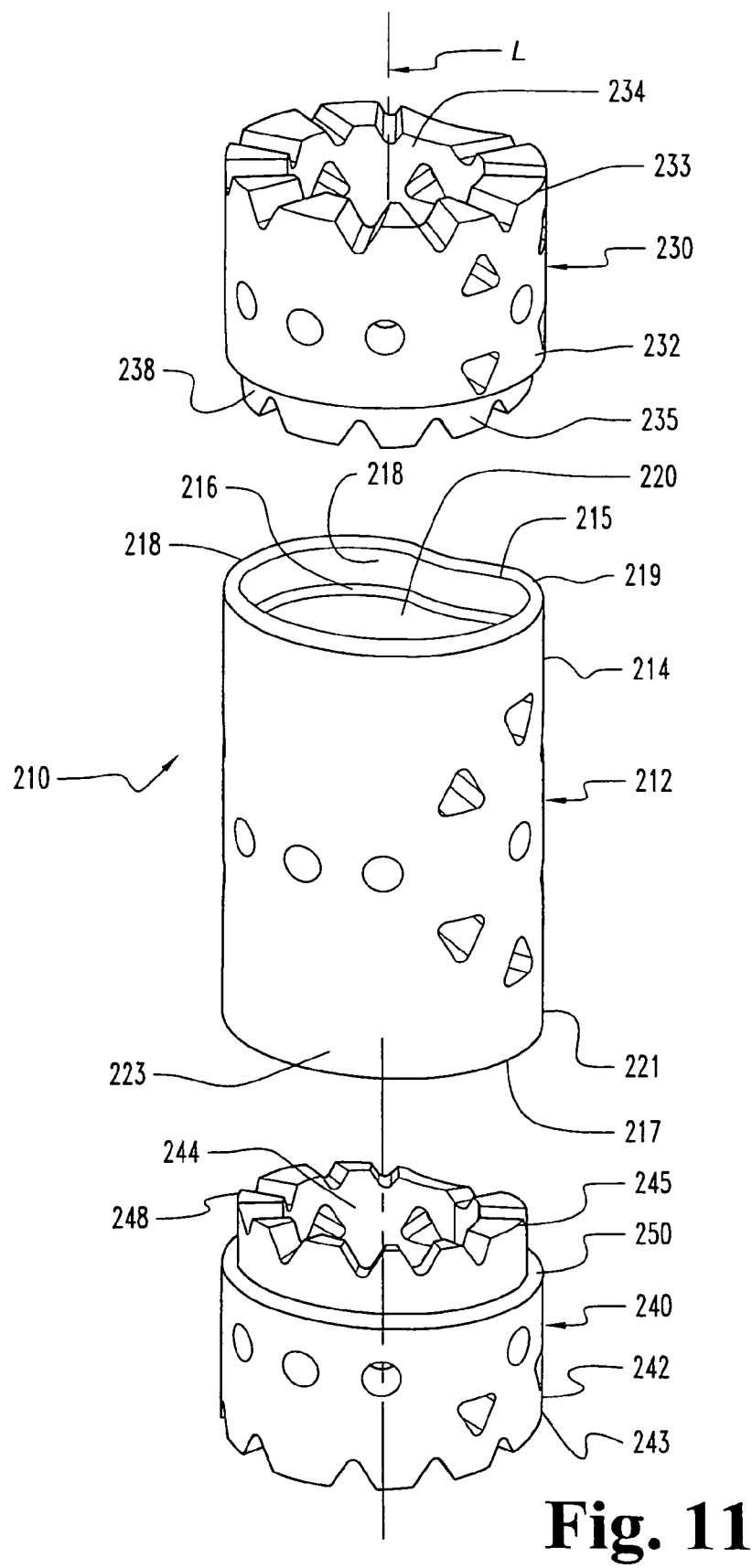
FIG. 11 is an exploded perspective view of another embodiment vertebral replacement device.

Referring now to FIG. 11, another embodiment vertebral replacement device 210 is shown. Device 210 includes a vertebral replacement or connecting member 212 having a body 214 extending between an upper end 219 and a lower end 221. Upper end 219 includes an upper extension 218 having an end surface 215 therearound. Extension 218 extends around a bearing surface 216 at the upper end of chamber 220. Bearing surface 216 is positioned below end surface 215 in chamber 220. Second end 217 similarly includes an extension 223 having an end surface 217, and a bearing surface (not shown) at the lower end of chamber 220 below end surface 217.

A first disc replacement or upper member 230 includes a body 232 having an upper end 233 and a lower end 235. Body 232 extends around a chamber 234. A second disc replacement or lower member 240 includes a body 242 having a lower end 243 and an upper end 245. Body 242 extends around a chamber 244. Lower member 240 includes an inset wall 248 extending around chamber 244, and a bearing surface 250 extending around body 242 below inset wall 248. Upper member 230 similarly includes an inset wall 238 and a bearing surface (not shown) extending around body 232 above inset wall 238.

When assembled, inset wall 238 of upper member 230 is received in chamber 220 of connecting member 212 with extension 218 extending around inset wall 238. Similarly, inset wall 248 of lower member 240 is received in chamber 220 of connecting member 212 with extension 223 extending around inset wall 248. It contemplated that end surface 215 can contact the bearing surface extending around inset wall 238, and that end surface 217 can contact bearing surface 250 extending around inset wall 248. Additionally or alternatively, the lower end of inset wall 238 can contact bearing surface 216 in chamber 220 at the upper end of connecting member 212, and the upper end of inset wall 248 can contact the bearing surface (not shown) in chamber 220 at the lower end of connecting member 212.

Connecting member 212 and/or upper and lower members 230, 240 could be provided with engaging members or a sleeve such as discussed above to prevent axial and/or rotational movement of upper and lower members 230, 240 relative to connecting member 212 when device 210 is assembled. In a further embodiment, connecting member 212 does not include the upper bearing surface 216 and the lower bearing surface in chamber 220 since extensions 218, 223 are not provided on connecting member 212. In this embodiment, inset walls 238 and 248 are received in chamber 220 at the respective end of connecting member 212, and end surfaces 215, 217 contact respective ones of the bearing surfaces extending around inset walls 238, 248.

Referring now to FIGS. 12-21, there is shown another embodiment vertebral replacement device 300. Vertebral replacement device 300 includes one or more upper or lower end or disc replacement members 400, 401 and one or more connecting or vertebral body members 310 engaged to disc replacement members 400, 401. Vertebral replacement device 300 has application in corpectomy procedures in which one or more vertebrae are removed, and in interbody fusion procedures where the device is positioned in a spinal disc space. In the illustrated embodiment, vertebral replacement device 300 includes three members stacked one upon the other. Other embodiments contemplate vertebral replacement devices comprising two members stacked one upon the other, and vertebral replacement devices comprising four or more members stacked one upon the other.

It is contemplated that vertebral body member 310 can be provided as a single unit or in multiple sections coupled to one another. Disc replacement members 400, 401 can be engaged at opposite ends of vertebral body member 310. It is further contemplated that one end of vertebral body member 310 can be configured to contact a vertebral endplate, and the opposite end engaged with a disc replacement member 400, 401 to form a two member stack. It is also contemplated that a pair of vertebral body members 310 can be engaged to respective upper and lower ends of a single disc replacement member 400, 401. The ends of the vertebral body members 310 opposite the disc replacement member 400, 401 can be configured to engage a vertebral endplate, or configured for engagement with a second disc replacement member 400, 401.

Figure 12:
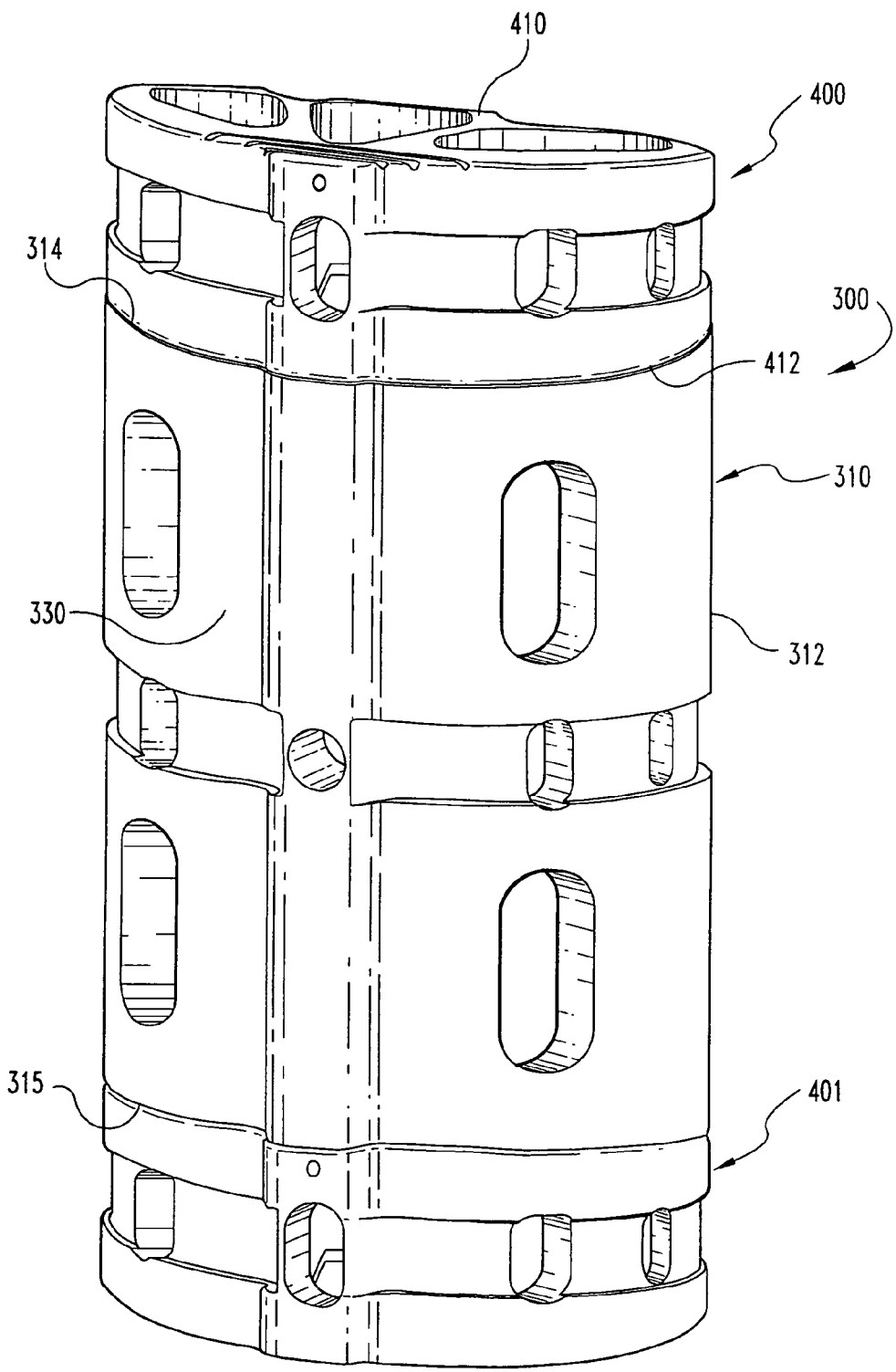
FIG. 12 is a perspective view of a vertebral replacement device according to another embodiment of the present invention.
Figure 13:
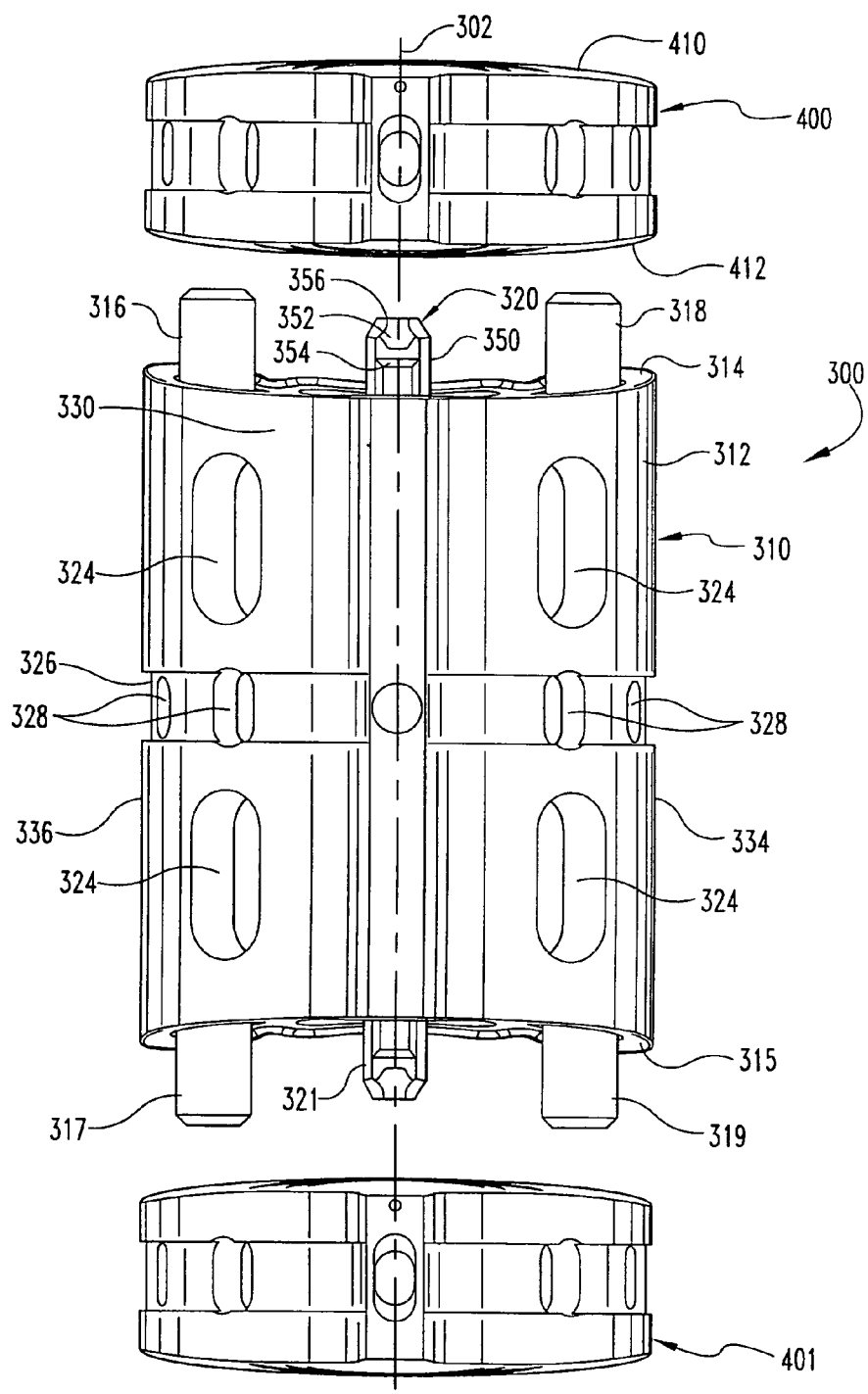
FIG. 13 is an exploded perspective view of the vertebral replacement device of FIG. 12.
Figure 14:
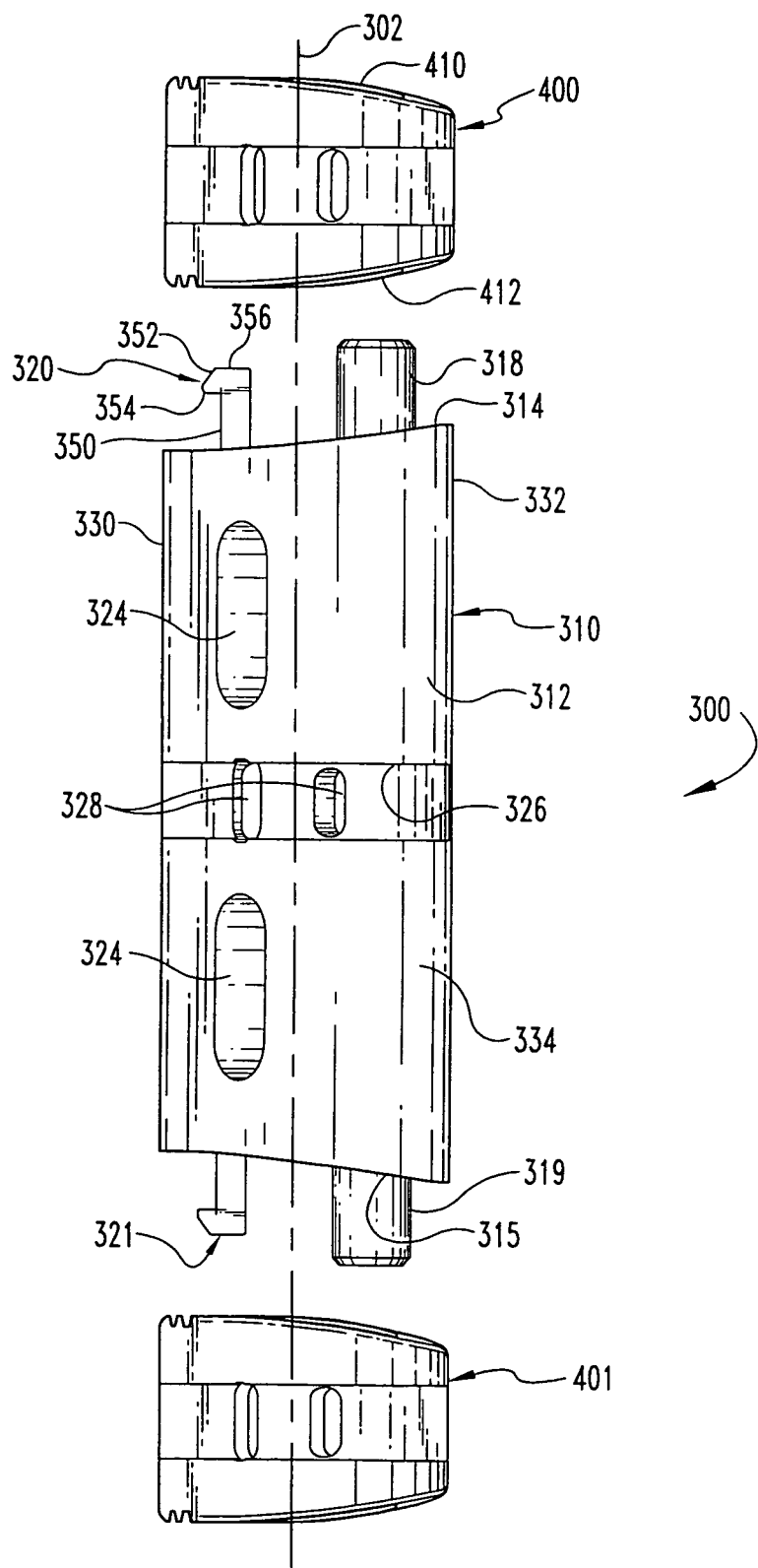
FIG. 14 is a side elevation exploded view of the vertebral replacement device of FIG. 12.
Figure 15:
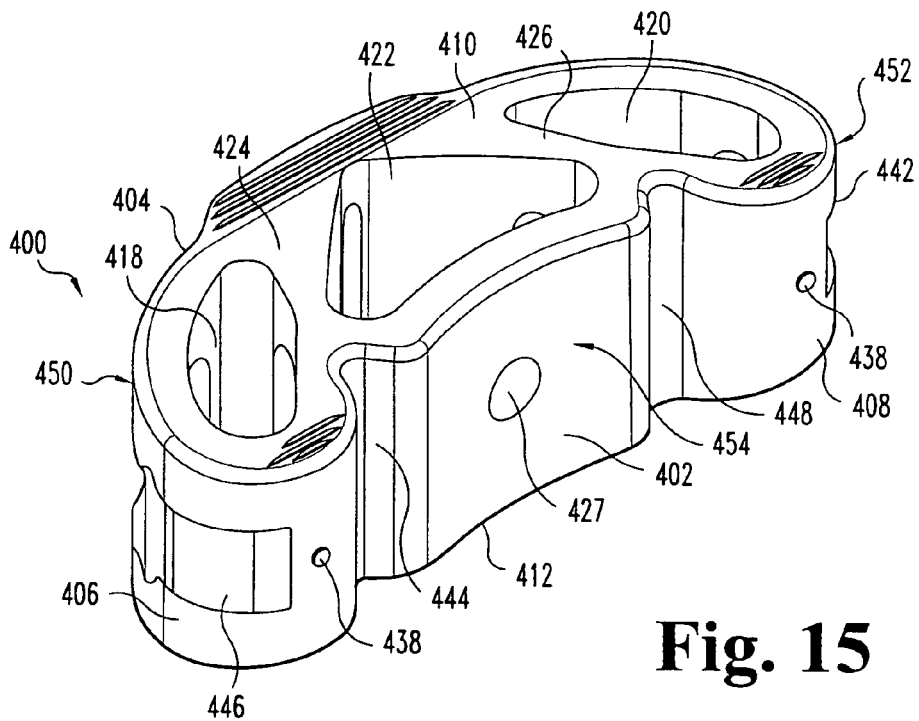
FIG. 15 is a perspective view looking toward a concavely curved wall of a disc replacement member comprising a portion of the device of FIG. 12.
Figure 16:
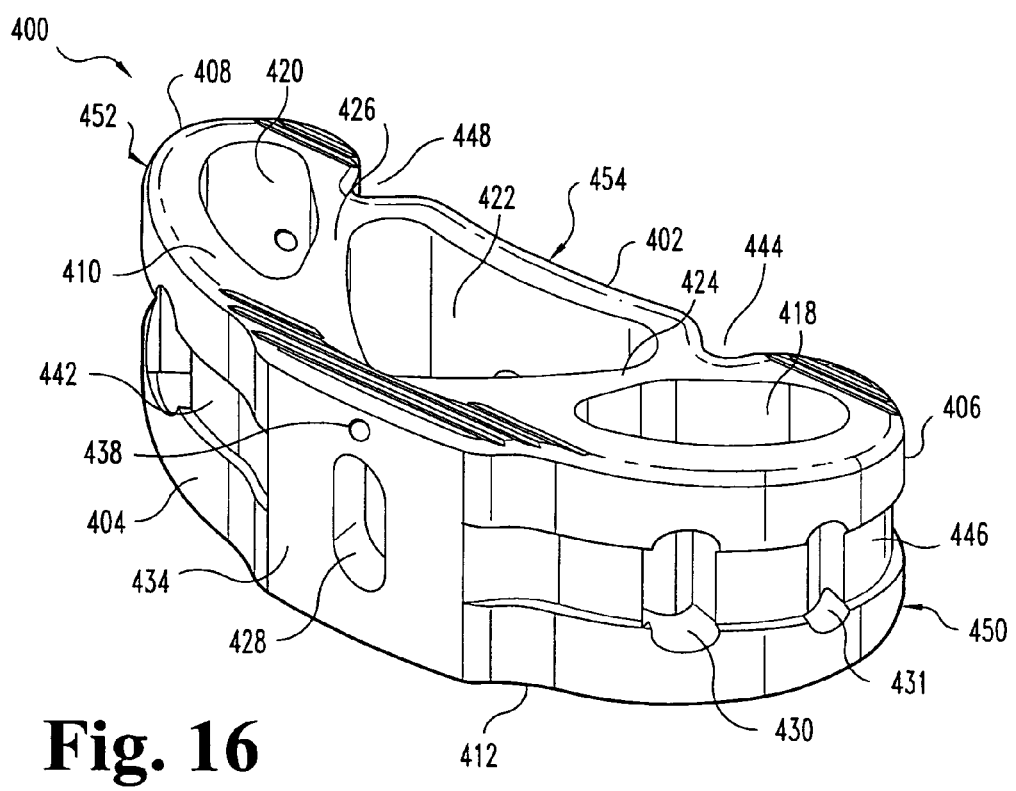
FIG. 16 is a perspective view looking toward a convexly curved wall of the disc replacement member of FIG. 15.
Figure 17:
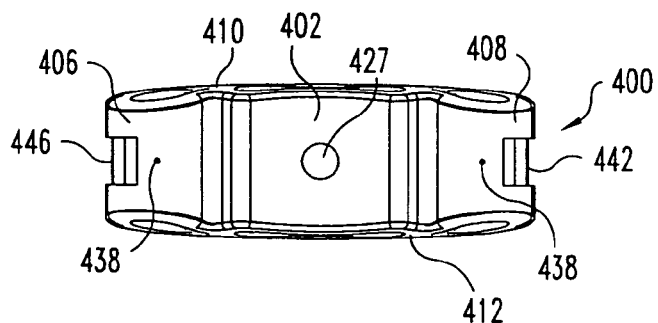
FIG. 17 is an elevation view looking at the concavely curved wall of the disc replacement member of FIG. 15.
Figure 18:
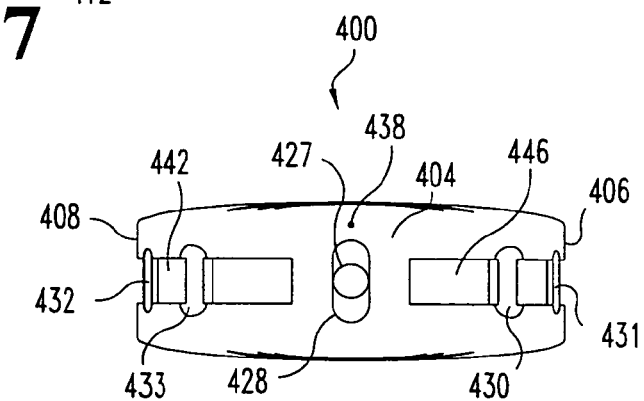
FIG. 18 is an elevation view looking at the convexly curved wall of the disc replacement member of FIG. 15.
Figure 19:
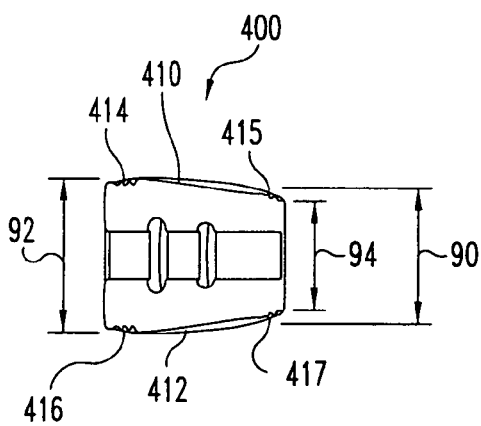
FIG. 19 is a plan view of the disc replacement member of FIG. 15.
Figure 20:
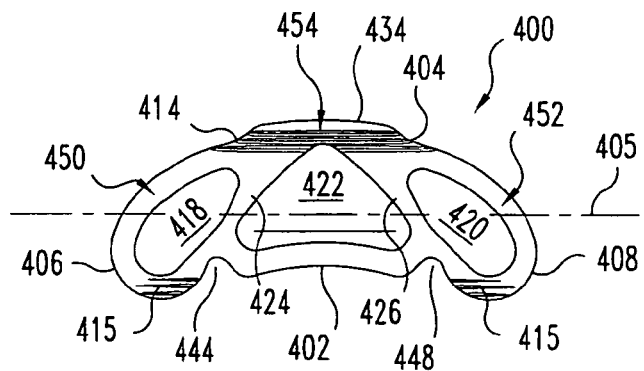
FIG. 20 is an end elevation view of the disc replacement member of FIG. 15.

In FIGS. 12-14 vertebral replacement device 300 extends along longitudinal axis 302 includes vertebral body member 310 having a body 312. A first or upper disc replacement member 400 is engaged at an upper end of a body 312 and a second or lower disc replacement member 401 is engaged at a lower end of body 312. Body 312 extends between an upper end surface 314 and a lower end surface 315. In the illustrated embodiment, end surfaces 314, 315 include a concave curvature in at least one direction transverse to longitudinal axis 302 to provide a solid bearing relationship with an adjacent convex surface of the disc replacement member 400, 401 positioned thereagainst.

Body 312 includes a wall extending between upper end surface 314 and lower end surface 315. The wall includes, in one contemplated implantation orientation, an anterior portion 330 and an opposite posterior portion 332. Opposite side or end portions 334, 336 extend between and interconnect anterior portion 330 and posterior portion 332. Other implantation orientations are contemplated where walls 330, 332, 334, 336 have other orientations relative to the patient. In the illustrated embodiment, end surfaces include smooth, uninterrupted surface profile that includes a first concave curvature between anterior portion 330 and posterior portion 332 as shown in FIG. 14, and a second concave curvature between end portions 334, 336, as shown in FIG. 13. The double concavity matches the surface profile of the end surface of the disc replacement member 400, 401 positioned thereagainst. The surface profile of the end surface of the disc replacement member 400, 401 can be selected to provide the desired fit with the patient's anatomy at the vertebral endplates.

Figure 21:
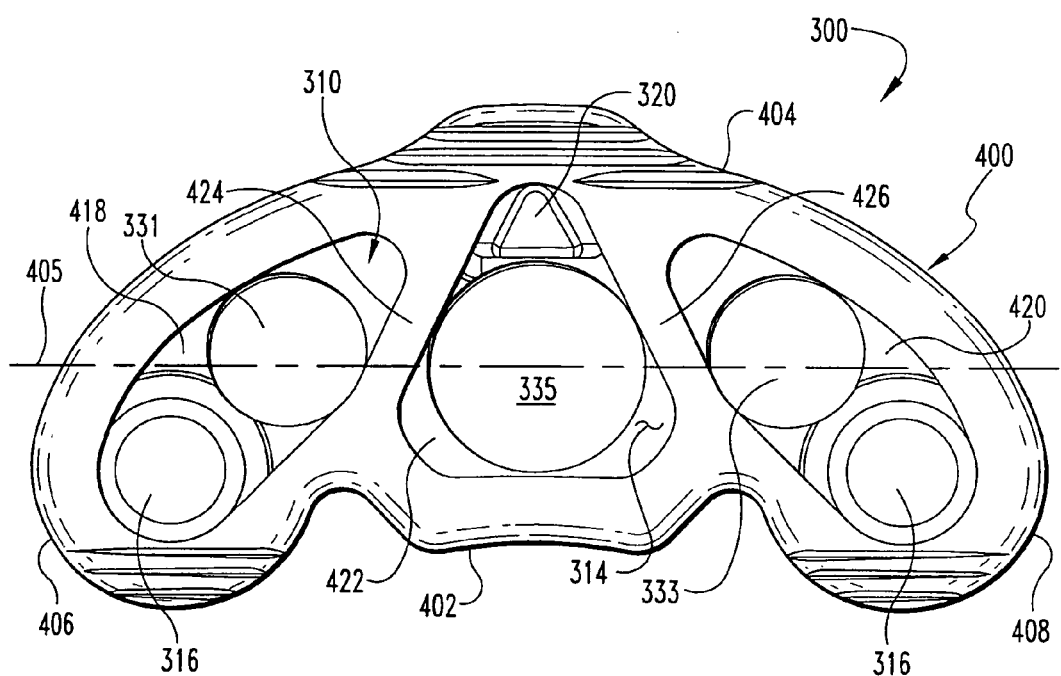
FIG. 21 is a plan view of the vertebral replacement device of FIG. 12.

In one form, body 312 includes a boomerang or banana shaped cross-section transverse to longitudinal axis 302, such as shown in FIG. 21. In this form, anterior wall portion 330 is convexly curved along its outer surface and posterior wall portion 332 is concavely curved along its outer surface. End wall portions 334, 336 are convexly curved and offset posteriorly relative to anterior portion 330, such as discussed with respect replacement member 400 below. Other shapes for body 312 are also contemplated such as discussed above with respect to device 10. The illustrated shape of vertebral replacement device 300 facilitates positioning in a space between vertebrae along a curved insertion path from a posterior-lateral approach such that, when finally positioned, bilateral support of the vertebrae is provided by vertebral replacement device 300.

Body 312 includes a groove 326 extending therearound mid-height along anterior wall portion 330 and end wall portions 334, 336. Groove 326 can facilitate attachment to an insertion instrument having an engagement portion adapted for positioning in groove 326. It is also contemplated that body 312 can be provided without groove 326. It is further contemplated that body 312 can be provided with one or more threaded openings, non-threaded openings, one or more receptacles or other structure for engagement of an insertion instrument with body 312.

Body 312 can include number of openings through its wall portions in communication with one or more chambers in body portion 312. In the illustrated embodiment, body 312 includes openings 328 in groove 326. Additional openings 324 are provided in anterior wall portion 330 above and below groove 326. Openings can also be provided in posterior wall portion 332 and/or end wall portions 334, 336 of body 312. In the illustrated embodiments, openings 324 are elongated and form an oval or racetrack shape along longitudinal axis 302. Openings 328 can also be elongated in the direction of longitudinal axis 302 and extend between the upper and lower sides of groove 326. The elongated openings 326, 328 maximize communication between the internal chamber or chambers of body 312 and the exterior of body 312 to facilitate bony incorporation of body 312 during fusion with bone growth material in body 312 and the bone growth material outside body 312. Other embodiments contemplate that body 312 can be provided with any number of wall openings in any shape, including circular, triangular, polygonal or curved openings. It is also contemplated that body 312 can be provided without any wall openings.

Posterior portion 332 of the wall of body 312 can includes one or more receptacles that are identical in shape to receptacles 444, 448 of end member 400 as discussed below. Such receptacles can extend along all or a portion of the length of body 312 between ends 314, 315.

Vertebral body member 310 includes a first engaging member 320 extending from upper end surface 314 along axis 302, and a second engaging member 321 extending from lower end surface 315 along axis 302. Engaging members 320, 321 can be identical to one another, and are described with reference to engaging member 320. Engaging member 320 includes a projection or engaging portion 352 and a stem 350 connected or integrally formed with end surface 314 of body 312. Stem 350 can include a thickness that allows engaging member 320 to deflect inwardly toward longitudinal axis 302 in response to a force applied to engaging portion 352. Engaging portion 352 projects outwardly from stem 350 away from longitudinal axis 302 in the illustrated embodiment. Engaging portion 352 includes a triangular shape tapering from a lower engaging surface 354 to an upper end 356, as shown in FIG. 13. Engaging portion can also slope toward axis 302 from engaging surface 354 to upper end 356, as shown in FIG. 14, to facilitate passage of the disc replacement member thereover.

Other configurations for engaging members 320, 321 are also contemplated. For example, engaging members 320, 321 can be provided with an engaging portion 352 in the form of a partially spherical or rounded nub, a receptacle, rectangular or polygonal shaped tab or projection. Engaging portion 352 can also correspond to the shape of the aperture, recess or other receptacle in which it is received when engaged to the corresponding disc replacement member 400, 401. Engaging members 320, 321 can also be a snap ring, collet, bayonet lock, or surface irregularity that resists axial movement of the engaged disc replacement member 400, 401 away from vertebral body member 310 along axis 302.

Vertebral body member 310 includes a first upper extension 316 and a second upper extension 318 extending from upper end surface 314 in the direction of longitudinal axis 302. Vertebral body member 310 also includes a first lower extension 317 and a second lower extension 319 extending from lower end surface 315 in the direction of longitudinal axis 302. These extensions are received in chambers of the adjacent disc replacement members 400, 401 and contact inner wall surfaces to resist lateral and rotational displacement of the disc replacement members 400, 401 relative to vertebral body member 310.

Referring further to FIGS. 15-20, further details regarding disc replacement members 400, 401 will be further discussed with reference to disc replacement member 400. While it is contemplated that disc replacement members 400, 401 can be identical to one another, identity is not required. It is also contemplated that only one disc replacement member 406 can be provided for removable engagement with vertebral body member 310. In addition to use with vertebral body member 310 as a vertebral replacement device, disc replacement member 400 can be separated from vertebral body member 310 and positioned in a spinal disc space as an interbody spacer. It is contemplated that disc replacement member 400 can be provided with a hollow interior or one or more openings that can be packed with bone growth material or other known substance and inserted into the disc space to promote bony fusion between adjacent vertebrae. Disc replacement member 400 can also be used in non-fusion procedures, or in fusion procedures where bone growth through the member is not contemplated.

Disc replacement member 400 can be provided with a boomerang or banana shape that is suited for insertion from a postero-lateral or uni-lateral approach into the disc space. It is also contemplated that disc replacement member 400 can be inserted in the disc space using any other techniques and instruments and other approaches to the disc space, such as lateral, anterior or antero-lateral approaches. While it is contemplated that vertebral body member 312 and disc replacement member 400 have the same shape when viewed along longitudinal axis 302, differing shapes for each member are also contemplated.

Disc replacement member 400 includes a body having a first end portion 450, a second end portion 452, and a middle portion 454 therebetween. When inserted into a disc space, for example, from a posterior-lateral approach, either of the end portions 450, 452 can be a leading end and the other a trailing end, depending on the orientation of disc replacement member 400 and the direction of insertion. A concave posterior wall 402 and an opposite convex anterior wall 404 extend along middle portion 454, and also along at least part of the corresponding side of first end portion 450 and second end portion 452. Disc replacement member 400 further includes an arcuate convexly curved first end wall 406 extending along first end portion 450 between posterior wall 402 and anterior wall 404. Disc replacement member 400 also includes an arcuate convexly curved second end wall 408 extending along second end portion 452 between posterior wall 402 and anterior wall 404. Disc replacement member 400 further includes a first end surface 410 and an opposite second end surface 412 extending between walls 402, 404, 406 and 408.

Disc replacement member 400 has a first height 90 at the medial portion of posterior wall 402 and a second height 92 at the medial portion of anterior wall 404. First end surface 410 and second end surface 412 have a convex curvature between the posterior and anterior walls 402, 404. Second height 92 is greater then first height 90 in order to correspond to the anatomy of the vertebral endplates on each side of the disc space at the contemplated insertion location for disc replacement member 400. First end wall 406 and second end wall 408 each include a height 94 that is less than first and second heights 90, 92. First end surface 410 and lower end surface 412 have a convex curvature between first end wall 406 and second end wall 408 as best shown in FIGS. 17-20. This double convex curvature substantially matches the double concave curvature of the adjacent vertebral endplates. Furthermore, the difference in heights between the upper and lower end surfaces at the anterior and posterior walls can be provided so as to establish lordosis when disc replacement member 400 is inserted in the disc space. Other embodiments contemplate that surfaces 410, 412 include a single convex curvature, or more than two convex curvatures.

First end surface 410 can further be provided with a number of first grooves 414 along anterior wall 404 and second grooves 415 along first and second end walls 406, 408. Second end surface 412 can be provided with a number of first grooves 416 along anterior wall 404 and second grooves 417 along first and second end walls 406, 408. Grooves 414, 415 and grooves 416, 417 increase frictional resistance between the adjacent vertebral endplate and the end surfaces 410, 412 to resist posterior and anterior migration of disc replacement member 400 in the disc space.

In order to provide avenues for bone growth through disc replacement member 400, the walls of disc replacement member 400 can be provided with a number of chambers opening at first end surface 410 and second end surface 412. In particular, first end portion 450 includes first chamber 418 and second end portion 452 includes second chamber 420. Middle portion 454 includes a middle chamber 422. A first strut 424 is located between first chamber 418 and middle chamber 422 and extends between posterior wall 402 and anterior wall 404. A second strut 426 is located between second chamber 420 and middle chamber 422 and extends between posterior wall 402 and anterior wall 404.

As further shown in FIG. 21, middle chamber 422 includes a triangular shape with the anterior apex of the triangle in communication with opening 428 along anterior wall 404. Engaging member 320 is positionable in the apex of middle chamber 422 so that engaging portion 352 engages in opening 428. It is contemplated that at least engaging surface 354 of engaging portion 352 engages wall 404 at the bottom of opening 428 to resist movement of disc replacement member 400 away from vertebral body member 310 along axis 302.

First and second chambers 418, 420 include an elongated ovoid shape sized to receive extensions 316, 318 therein adjacent a posterior wall of the chamber. Accordingly, engaging member 320 extends along an inner surface of anterior wall 404, and extensions 316, 318 are each offset from engaging member 320 on the opposite sides of central axis 405 to contact inner surfaces of posterior wall 402 and/or end walls 406, 408 to resist rotation of disc replacement member 400 about longitudinal axis 302. Vertebral body member 310 includes a first chamber or passage 331 in communication with first chamber 418, a second chamber or passage 333 in communication with second chamber 420, and a central chamber or passage 335 in communication with middle chamber 422. Chambers 331, 333, 335 can extend through vertebral body member 310 between end surfaces 314, 315 to provide avenues for bone growth.

In the illustrated embodiment, extensions 316, 318 are cylindrical posts sized and shaped to be intimately received in posterior portions of chambers 418, 420. Engaging member 320 is a cylindrical post with a triangular cross-section for receipt in the anterior apex of chamber 422. Other embodiments contemplate other forms for engaging member 320 and extensions 316, 318. For example, extensions 316, 318 could be sized to substantially occupy the entire first and second chamber 418, 420 in which it is positioned. Additional extensions could be provided from vertebral body member 310 that are positionable in middle chamber 422. In another form, one or more of the struts 424, 426 could be eliminated, and one or more extensions provided that extend along a portion or substantially along the entire inner wall surface of disc replacement member 400. Alternatively or additionally to the illustrated extensions 320, one or more extensions 320 could be positioned about end surface 314 for engagement with other openings in the walls of disc replacement member 400.

Referring back to FIGS. 15-20, additional details regarding disc replacement member 400 will be discussed. Posterior wall 402 includes a posterior opening 427 along middle portion 454, and anterior wall 404 includes an anterior opening 428 along middle portion 454. In the illustrated embodiment, posterior wall opening 427 is circular and anterior wall opening 428 is oval or racetrack shaped and elongated in the direction between upper end surface 410 and lower end surface 412; however, other shapes for openings 427, 428 are also contemplated, including circular and non-circular shapes. First end portion 450 includes first and second wall openings 430, 431 in anterior wall 404, and second end portion 452 includes first and second wall openings 432, 433 in anterior wall 404. In the illustrated embodiment, openings 430, 431 and 432, 433 are oval or racetrack shaped and elongated in the direction between first end surface 410 and lower end surface 412; however, other shapes for openings 430, 431 and 432, 433 are also contemplated.

Anterior wall 404 includes an offset portion 434 that is offset anteriorly with respect to the remaining portions of anterior wall 404 extending from either side thereof. Anterior offset portion 434 provides additional bearing support area for the vertebrae and additional strength and rigidity to the body of disc replacement member 400. A number of radiographic markers 438 can also be provided in disc replacement member 400 to facilitate X-ray assessment of the locating and positioning of disc replacement member 400 in the patient's body. Such markers are particularly useful for a disc replacement member 400 made from radiolucent material. In the illustrated embodiment, markers 438 are provided at the midline of anterior wall 404 at the anterior-most point defined by offset portion 434. Markers 438 are also provided at the posterior-most points of first end wall 406 and second end wall 408. Positioning markers 438 at these locations provides an indication of the anterior and posterior placement of disc replacement member 400 in the disc space, and also an indication of the lateral placement of disc replacement member 400 in the disc space. Alignment of the end wall markers 438 in a lateral X-ray indicates proper orientation of disc replacement member 400 in the disc space in the A-P direction.

Disc replacement member 400 includes a recessed area 446 extending along first end wall 406 and a portion of anterior wall 404. Disc replacement member 400 also includes a recessed area 442 extending along second end wall 408 and a portion of anterior wall 404. Recessed areas 442, 446 are located in the respective wall portions mid-height between upper bearing surface 410 and lower bearing surface 412. Recessed surfaces 442, 446 are configured to receive a portion of an implant insertion instrument and to facilitate grasping of the implant, as discussed further below.

The symmetrical shape of disc replacement member 400 allows disc replacement member 400 to be inserted into the disc space from a unilateral approach taken on either side of the spinous process, and by grasping either of first end portion 450 or second end portion 452 with an insertion instrument.

Disc replacement member 400 is provided with a first inserter instrument engaging receptacle 444 at first end portion 450 and a second inserter instrument engaging receptacle 448 at second end portion 452. Each of the engaging receptacles 444, 448 are configured along with adjacent recessed areas 442, 446 for engagement with an implant inserter instrument. Body 312 can similarly be provided with receptacles aligned with receptacle 444, 448 in the stacked configuration that can be engaged with an implant insertion instrument.

Examples of insertion instruments for inserting disc replacement members 400, 401 and/or vertebral replacement device 300 are provided in U.S. patent application Ser. No. 10/120,104, which is incorporated herein by reference in its entirety. First end wall 406 and second end wall 408 could also include a threaded hole for engagement with an inserter. In the illustrated embodiment, engaging receptacles 444, 448 are in the form of grooves that extend between first end surface 410 and second end surface 412. Each of the grooves is aligned with a corresponding one of the first strut 424 and second strut 426. First strut 424 and second strut 426 provide bearing support to resist application of forces applied to the implant wall by an insertion instrument positioned in the respective engaging receptacle 444, 448.

Vertebral replacement device 300 includes an axis 405 extending through its center in the direction between first end wall 406 and second end wall 408, as shown in FIG. 21. Axis 405 is equal distance from the most posterior point on first end wall 406 and the most posterior point on second end wall 408. First end wall 406 is offset to the posterior side of axis 405, and second end wall 408 is offset to the posterior side of axis 405. Similarly, axis 405 is equal distance from the most posterior point on first end wall portion 334 and the most posterior point on second end wall portion 336 of body 312. The offset in the first and second ends of disc replacement member 400 and vertebral body member 310 facilitates the controlled insertion of vertebral replacement device 300 along a curved insertion path.

Referring now to FIGS. 22-23, there is shown another embodiment vertebral replacement device 500. Vertebral replacement device 500 includes one or more upper or lower end or disc replacement members 600, 601 and one or more connecting or vertebral body members 510 engaged to disc replacement members 600, 601. Vertebral replacement device 500 has application in corpectomy procedures in which one or more vertebrae are removed. Applications in disc space replacement and interbody fusion procedures are also contemplated. In the illustrated embodiment, vertebral replacement device 500 includes three members stacked one upon the other. Other embodiments contemplate two member stacks, or stacks comprising four or more members.

It is contemplated that vertebral body member 510 can be provided as a single unit or in multiple sections coupled to one another. Disc replacement members 600, 601 can be engaged at opposite ends of vertebral body member 510. It is further contemplated that one end of the vertebral body member 510 can be configured to contact a vertebral endplate, and the opposite end engaged with a disc replacement member 600, 601. It is also contemplated that a pair of vertebral body members 510 can be engaged to respective upper and lower ends of a disc replacement member 600, 601. The ends of the vertebral body members 510 opposite the disc replacement member 600, 601 can be configured to engage a vertebral endplate, or configured for engagement with a second disc replacement member 600, 601.

Referring further to FIGS. 24-26, vertebral replacement device 500 extends along longitudinal axis 502 and includes vertebral body member 510 having a body 512. A first or upper disc replacement member 600 is engaged at an upper end of body 512 and a second or lower disc replacement member 601 is engaged at a lower end of body 512. Body 512 extends between an upper end surface 514 and a lower end surface 515. Body 512 includes walls extending between upper end surface 514 and lower end surface 515. The walls include a first end wall 530 and an opposite second end wall 532. Opposite side walls 534, 536 extend between and interconnect first end wall 530 and second end wall 532.

In one form, body 512 includes a generally rectangular shape transverse to longitudinal axis 502, such as shown in FIG. 26. In the illustrated embodiment, end walls 530, 532 are generally parallel with one another, and side walls 534, 536 are generally parallel with one another. Adjacent walls can be connected with beveled portions or curved portions to eliminate abrupt edges between the walls at the corners of body 512. Other shapes for body 512 are also contemplated as discussed herein. In one application, side walls 534, 536 are oriented in the anterior-posterior direction when device 10 is positioned between vertebrae. End walls 530, 532 are shorter than side walls 530, 532 such that the width of between side walls 534, 536 is less than the half of the supported vertebral endplates in the medial-lateral direction. Accordingly, bilateral support of the vertebrae is provided by positioning a pair of vertebral replacement devices 10 in the space between the vertebrae with the side walls 534, 536 of each device oriented in the anterior-posterior direction. Other applications contemplate that side walls 534, 536 can be positioned in other orientations in the space between vertebrae, including medial lateral orientations and oblique orientations.

Upper and lower end surfaces 514, 515 each include a surface profile that facilitates stacking of disc replacement members 600, 601 thereon to provide a stable stacking arrangement. In the illustrated embodiment, upper end surface 514 of body 512 includes a concave curvature between end walls 530, 532. Similarly, lower end surface 515 includes a concave curvature between end walls 530, 532. Upper and lower end surfaces 514, 515 are not curved between side walls 534, 536. Upper and lower end surfaces 514, 515 are smooth and do not include surface interruptions. As shown in FIGS. 22-23, disc replacement members 600, 601 include a convex curvature that allows the disc replacement member to be fully supported by the respective end surfaces 514, 515 between end walls 530, 532 and side walls 534, 536. Other embodiments contemplate other configurations for upper and lower end surfaces 514, 515 as discussed herein.

Body 512 can include number of openings through its wall structure in communication with one or more chambers 526 in body 512. In the illustrated embodiment, body 512 includes a pair of openings 528 in side wall 534. Openings 528 are positioned on opposite sides of axis 302, and one opening 528 is offset toward end surface 514 and the other opening is offset toward end surface 515. Side wall 536 can be provided with similarly located openings. Openings can also be provided in end walls 530, 532, such as opening 524 shown in end wall 532. In the illustrated embodiments, opening 524 is centrally positioned in end wall 532. It is contemplated that any one or combination of the openings 524, 528 can be threaded, non-threaded and/or non-circular. Any one or combination of the openings 524, 528 can be engaged with an insertion instrument to facilitate insertion of vertebral replacement device 500 in the space between vertebrae.

Chamber 526 extends through body 512 and opens at end surfaces 514, 515. The openings 524, 528 can communicate with chamber 526 to provide avenues for bone growth through the wall of body 512. Other embodiments contemplate that body 512 can be provided with any number of openings in any shape, including circular, non-circular, triangular, polygonal or curved openings. It is also contemplated that body 512 can be provided without any openings. Body 512 can also be provided without a chamber 526, but rather a solid body structure. Body 512 can further be provided with multiple chambers or openings extending therethrough between end surfaces 514, 515.

Vertebral body member 510 includes engaging members 520, 521 extending from upper end surface 514 adjacent respective ones of the side walls 534, 536. Similarly, engaging members 523, 525 extend from lower end surface 515 adjacent respective ones of the side walls 534, 536. Engaging members 520, 521, 523, 525 include a reduced thickness and are aligned with the inner wall surface of body 512 defining chamber 526. Accordingly, end surfaces 514, 515 extend along the outer side of engaging members 520, 521, 523, 525.

Engaging members 520, 521, 523, 525 can be identical to one another, and like elements are designated with the same reference numerals. Engaging members 520, 521, 523, 525 each include a stem 550 connected or integrally formed with the respective end surface 514, 515 of body 512 as shown in FIG. 27. A projection or engaging portion 552 extends outwardly from the stem 550. Stem 550 can include a reduced thickness relative to the wall with which it is formed to allow engaging members 520, 521, 523, 525 to deflect inwardly toward the adjacent engaging member in response to a force applied to engaging portion 552. Engaging portion 552 projects outwardly toward the respective adjacent side wall from stem 550. Engaging portion 552 includes a truncated cylindrical shape, as best shown in FIGS. 24-27. Truncated portion 553 of engaging portion 552 facilitates passage of a disc replacement member 600, 601 thereover. Engaging portion 552 includes an engaging surface 554 that contacts the side wall of disc replacement member 600, 601 in the adjacent hole 624, 624 to resist axial displacement of the disc replacement member Other configurations for engaging portions 552 are also contemplated, such as a partially spherical or rounded nub, a receptacle, rectangular or polygonal shaped tab or projection. The portion of engaging portion 552 opposite truncated portion 553 can correspond to the shape the side wall aperture of disc replacement member 600, 601 in which it is received. Engaging members 520, 521, 523, 525 can also include a snap ring, collet, bayonet lock, or surface irregularity that resists axial movement of the engaged disc replacement member 600, 601 away from vertebral body member 510 along axis 502.

Vertebral body member 510 includes upper extensions 560, 562 extending from upper end surface 514 adjacent respective ones of the end walls 530, 532. Vertebral body member 510 further includes lower extensions 564, 566 extending from lower end surface 515 adjacent respective ones of the end walls 530, 532. As discussed further below, extensions 560, 562, 564, 566 are positionable in the chamber of the adjacent disc replacement member 600, 601 to provide lateral and torsional stability when the disc replacement member 600, 601 is stacked on vertebral body member 510.

Figure 28:
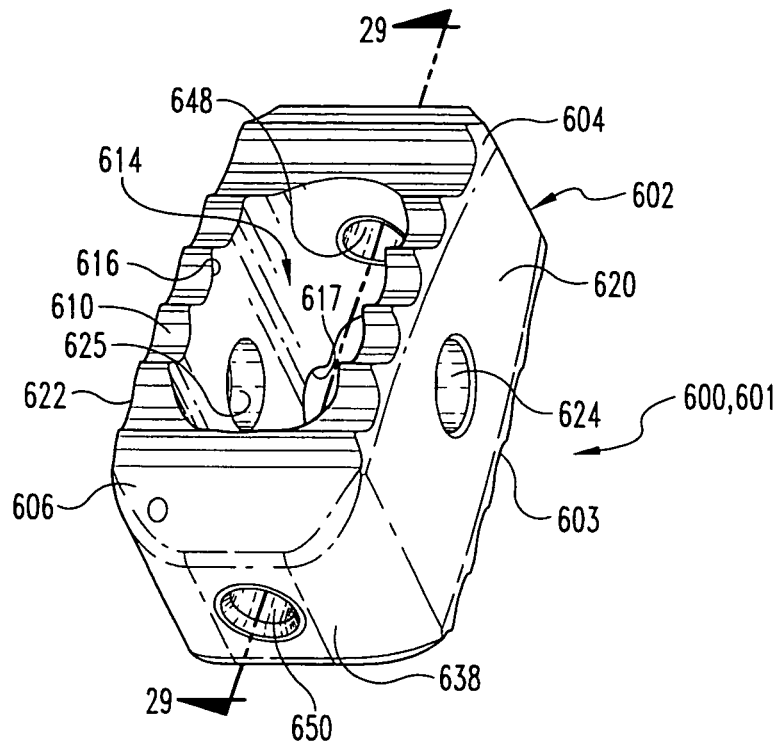
FIG. 28 is a perspective view of a disc replacement member comprising a portion of the vertebral replacement device of FIG. 22.
Figure 29:
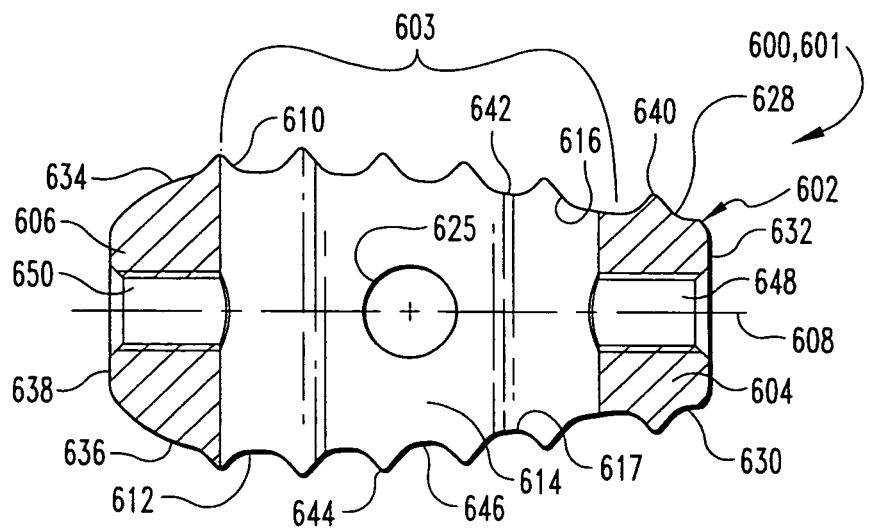
FIG. 29 is a section view of the disc replacement member of FIG. 28 through line 29-29.

Referring now to FIGS. 28 and 29, disc replacement member 600, 601 will be further discussed. Disc replacement members 600, 601 can be secured to vertebral body member 510, and are adapted for insertion in isolation into a spinal disc space between adjacent vertebrae to promote fusion of the vertebrae and restore disc space height. Disc replacement members 600, 601 can be identical, and include an elongate body 602 defining a longitudinal axis 608, a first end portion 604, and a second end portion 606. At least one of end portions 604, 606 includes opposed upper and lower bearing surfaces adapted to bear against the endplates of the supported vertebrae. In one embodiment, body 602 is provided to have a substantially rectangular cross-section when viewed in section in the direction of longitudinal axis 608.

Body 602 includes central portion 603 that extends from first end portion 604 to second end portion 606. Body 602 includes an upper surface 610 and an opposite lower surface 612 defining chamber 614 therebetween. Upper surface 610 and lower surface 612 can be convexly curved along longitudinal axis 608 substantially mate with the natural curvature of corresponding facing endplate surfaces of adjacent vertebrae. Thus, the convex configuration of upper surface 610 and lower surface 612 facilitates locating the disc replacement members 600, 601 approximately in the anterior-posterior middle of the endplate of the adjacent vertebral body. The convex upper and lower surfaces 610, 612 can inhibit expulsion of the surgically implanted member 600, 601 by providing a maximum height that is greater than the height of a surgically prepared entrance to the spinal disc space. In the illustrated embodiment, upper surface 610 and lower surface 612 are provided with a number of arcuate concave portions 642 longitudinal axis 608, although a smooth surface profile is also contemplated.

Further, upper surface 610 includes at least one opening 616 extending into chamber 614. Similarly, lower surface 612 includes at least one opening 617 into chamber 614. The perimeter of both the upper and lower surfaces 610, 612 is substantially continuous and uninterrupted. Chamber 614 is provided to receive a graft of osteogenetic material, such as spongy bone or other material favoring bone growth, including synthetic bone media. Therefore, the curvilinear configuration of upper surface 610 and lower surface 612 and their associated openings 616, 617 allow interpenetration of the cancellous bone revealed in the surgically prepared intervertebral space of adjacent vertebrae. Interpenetration of the cancellous bone of the vertebra enhances the intimate contact and interdiffusion of osteogenic material initially deposited in chamber 614 with the cancellous bone tissue and greatly enhances the potential for bone growth.

Body 602 can also include parallel side walls 620 and 622 extending between upper surface 610 to lower surface 612, and between end portions 604, 606. Side walls 620 and 622 can include openings 624 and 625, respectively, providing communication into chamber 614 to further enhance interdiffusion of the osteogenic material in chamber 614 with cancellous bone tissue and material outside chamber 614. The opposite openings 624, 625 are also engageable by respective ones of the engaging members 520, 521 or engaging members 523, 525 when disc replacement member 600, 601 is stacked on the corresponding end of vertebral body member 510. It is contemplated that upper surface 610 and lower surface 612 provide a substantially uniform height from side wall 620 to side wall 622 in when viewed orthogonally to longitudinal axis 608. Other embodiments contemplate side walls 620, 622 that define an uneven height for body 602 orthogonally to longitudinal axis 608.

First end portion 604 includes a first bearing surface 628, an opposite second bearing surface 630, and a first end wall 632 extending therebetween. First bearing surface 628 and second bearing surface 630 can engage surfaces of cortical bone endplates on adjacent vertebral bodies. When inserted within a prepared intervertebral space, first bearing surface 628 and second bearing surface 630 bear against cortical bone tissue proximate to the posterior portion of the vertebral space. Second end portion 606 includes a first bearing surface 634, an opposite second bearing surface 636, and a first end wall 638 extending therebetween. First bearing surface 634 and second bearing surface 636 engage surfaces of cortical bone endplates on adjacent vertebral bodies. Ion one application, when inserted within the prepared intervertebral space first bearing surface 634 and second bearing surface 636 bear against cortical bone tissue proximate to the anterior portion of the intervertebral space. Bearing surfaces 628, 630, 634, 636 can sustain the compressive forces associated with normal activity and resist receding into the sponge-like cancellous bone tissue of the vertebral body. Surfaces 610, 612, 628, 630, 634, 636 can be planar, curved or otherwise configured to conform to the profile of the vertebral anatomy against which it is to be positioned. The desired disc height can be maintained for an extended time period while bone fusion progresses. The bearing surfaces can be tapered or offset along longitudinal axis 608 to provide a desired angle between the vertebrae, or can be non-tapered.

The upper bearing surfaces of body 602 include anti-expulsion features 640, formed by arcuate grooves 642 in the upper surfaces of body 602. The lower bearing surfaces of body 602 include anti-expulsion features 644, formed by arcuate grooves 646 in the lower surfaces of body 602. In one embodiment, grooves 642, 646 extend transversely to longitudinal axis 608.

First end portion 604 includes tool-engaging portion 648. Tool-engaging portion 648 can be provided with a variety of features adapted to engage an insertion tool for insertion of disc replacement devices into the space between vertebrae. For example, tool-engaging portion 648 can include a variety of indents and openings, which may or may not be threaded, to engage correspondingly configured features on an insertion instrument and/or manipulation accessory (not shown) to facilitate implantation and/or movement of disc replacement member 600, 601 in the space between vertebrae. Second end portion 606 includes tool-engaging portion 650. Tool-engaging portion 650 can be provided with a variety of features adapted to engage an insertion tool for insertion of disc replacement devices into the space between vertebrae. For example, tool-engaging portion 650 can include a variety of indents and openings, which may or may not be threaded, to engage correspondingly configured features on an insertion instrument and/or manipulation accessory (not shown) to facilitate implantation and/or movement of disc replacement member 600, 601 in the space between vertebrae from an approach opposite that used with tool engaging portion 648.

Disc replacement members 600, 601 can be assembled with vertebral body member 510, as shown in FIGS. 22 and 23, to provide vertebral replacement device 500. Engaging members 520, 522 extend into chamber 614 and engage side wall holes 624, 625, respectively, with engaging portions 552. The truncated portions 553 of engaging portions 552 facilitate passage of the inner surface of side walls 620, 622 along the outwardly facing surfaces of engaging portions 552, and deflect engaging members 520, 521 inwardly toward one another. When engaging portions 552 are aligned with the respective side wall openings 624, 625, engaging members 520, 521 return toward their pre-stacked configuration and engage the adjacent side wall opening 624, 625 to axially secure disc replacement member 600 to vertebral body member 510 and resist movement of disc replacement members 600, 601 away from vertebral body member 510. Disc replacement member 601 is similarly secured to engaging members 523, 525 at the opposite end of vertebral body member 510.

When stacked on vertebral body member 510, the lower bearing surface 612 of disc replacement member 600 is supported by upper end surface 514, and the upper bearing surface 610 of disc replacement member 601 is supported by lower end surface 515. Anti-expulsion features 644 of disc replacement member 600 bear against and are supported by upper end surface 514, and anti-expulsion features 640 of disc replacement member 601 bear against and are supported by lower end surface 515. The bearing relationship resists axial movement of disc replacement members 600, 601 toward vertebral body member 510. Grooves 642, 646 are spaced from the respective end surfaces 514, 515 and provide avenues for bone growth between vertebral body member 510 and disc replacement members 600, 601.

In addition to the stability provided by engaging members 520, 520, 523, 525, rotational or torsional stability between disc replacement members 600, 601 and vertebral body member 510 is provided with extensions 560, 562, 564, 566. Extension 560 contacts the inner wall surface 607 of disc replacement member 600 adjacent second end portion 606, and extension 562 contacts the inner wall surface 605 of disc replacement member 600 adjacent first end portion 604. The arcuate, semi-circular configuration of extensions 560, 562 also provides contact with the inner wall surface along side walls 620, 622 of disc replacement member 600. Accordingly, lateral and rotational displacement of the disc replacement member 600 relative vertebral body member 510 is resisted by contact between the inner walls surfaces of disc replacement member 600 and extensions 560, 562. Disc replacement member 601 is similarly engaged with extensions 564, 566 to provide lateral and rotational stability with vertebral body member 510.

Figure 30:
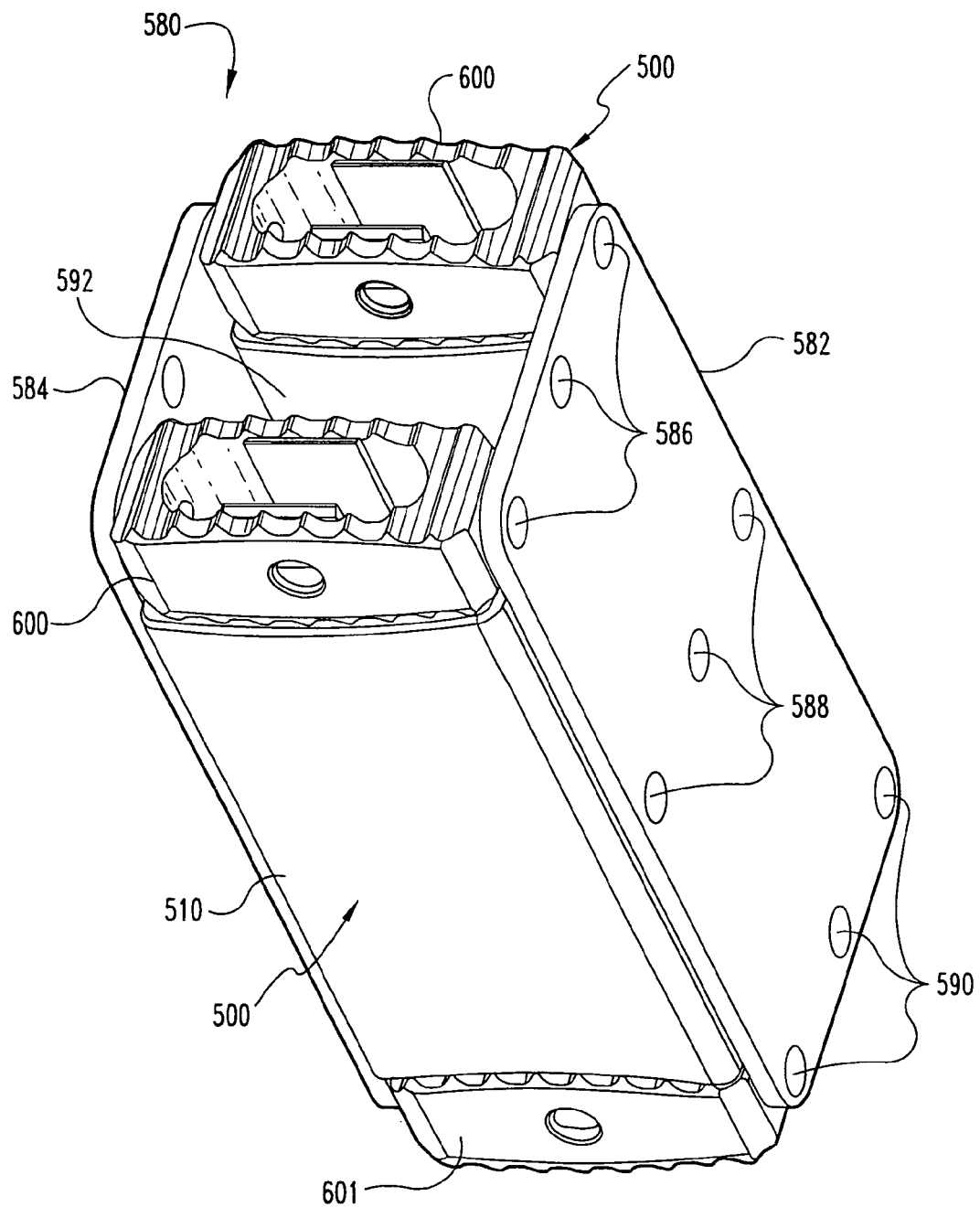
FIG. 30 is a perspective view of an assembly including a pair of vertebral replacement devices of FIG. 22.

Vertebral replacement devices 500 can be placed in isolation in a space between vertebrae, or multiple vertebral replacement devices can be positioned in a space between adjacent vertebrae. In some applications, the multiple vertebral replacement devices 500 can be secured to one another to provide further stability. Referring now to FIG. 30, a vertebral replacement system 580 includes a pair of vertebral replacement devices 500 positioned adjacent one another. Vertebral replacement devices 500 are coupled to one another with connecting systems 582, 584. Connecting systems 582, 584 can each be in the form of a plate having a number of apertures located to receive fasteners 586, 588, 590 to secure the respective plates to opposite ends of vertebral replacement devices 500. Connecting systems 582, 584 also have application with the other vertebral replacement devices discussed herein.

In the illustrated embodiment, connecting system 582 includes apertures through the plate to receive fasteners 586 to engage the tool engagement portions 648 at one end of disc replacement member 600 of each of the vertebral replacement devices 500. Connecting system 584 can be also provided with apertures through the plate to receive fasteners 586 to engage the opposite tool engaging portion 650 of disc replacement member 600. Fasteners 590 are received through apertures of the plate of connecting system 502 to engage the tool engagement portion 648 at one end of disc replacement member 601 of each of the vertebral replacement devices 500. Connecting system 584 can be provided with apertures and fasteners to engage the opposite tool engaging portion 650 of disc replacement members 601. Fasteners 588 are positioned through apertures of the plate of connecting system 582 to engage openings 524 at one end of vertebral body member 510 of each of the vertebral replacement devices 500. Connecting system 584 can also be provided with apertures and fasteners to engage an opposite opening of vertebral replacement members 510.

Vertebral replacement system 580 includes a space 592 between vertebral replacement devices 500 to provide a bone fusion path. Space 592 can be provided in addition to or in lieu of the chambers extending through vertebral replacement devices 500. Alternatively, a third vertebral replacement device can be positioned in space 592 and secured to connecting systems 582, 584 with middle fasteners 586, 588, 590.

Figure 31:
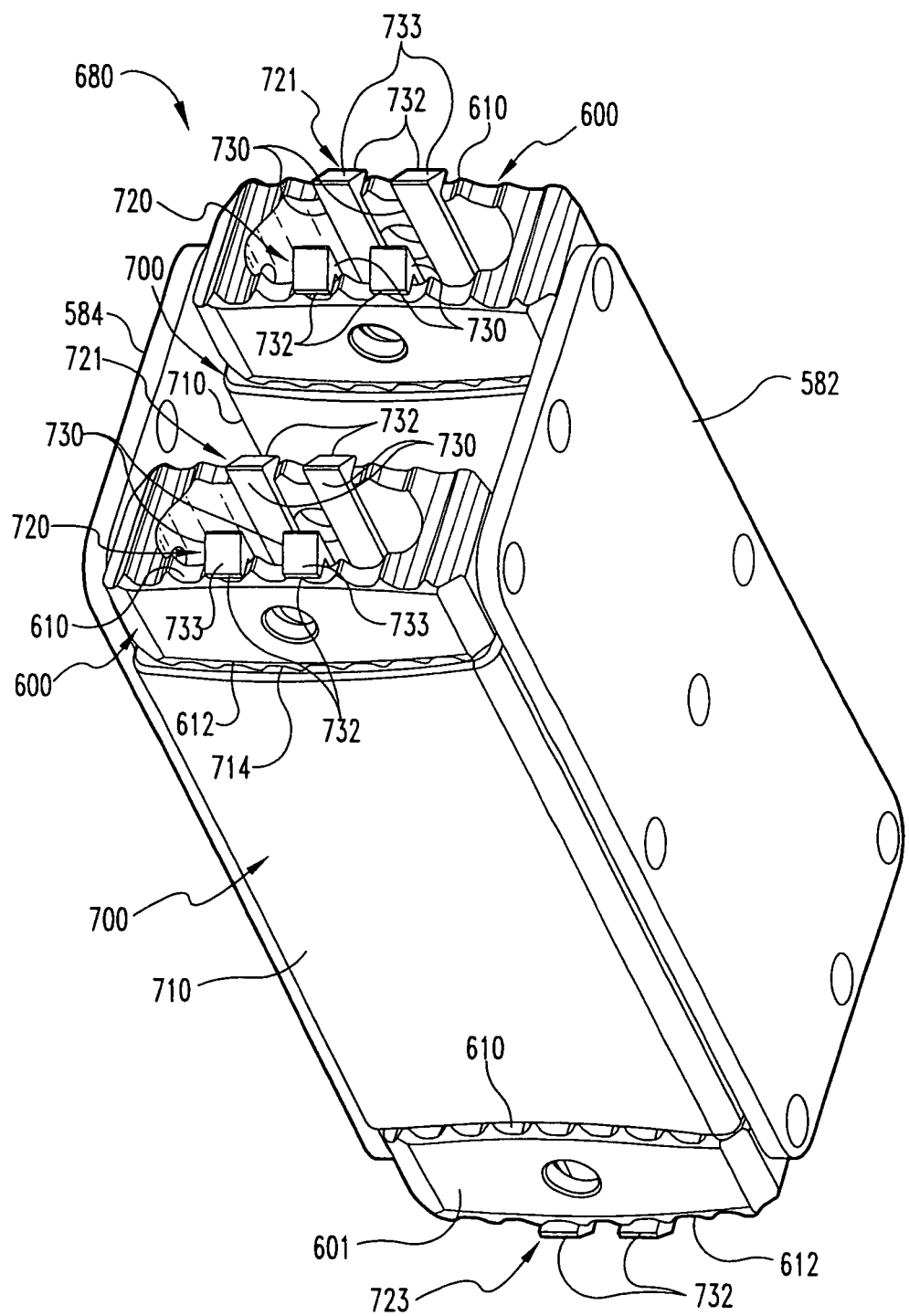
FIG. 31 is a perspective view of another embodiment assembly comprising another embodiment of the vertebral replacement device of FIG. 22.

In FIG. 31 there is shown another embodiment vertebral replacement system 680 similar to vertebral replacement system 580 that includes a pair of side-by-side vertebral replacement devices 700 connected with connecting systems 582, 584. Vertebral replacement devices 700 include another embodiment vertebral body member 710 and opposite disc replacement members 600, 601. Vertebral replacement member 710 can be identical to vertebral body member 510 discussed above, but includes another embodiment engaging members 720, 721, 723, and also a fourth engaging member (not shown). Engaging members 720, 721, 723 are engaged to the upper and lower surfaces of disc replacement members 600, 601. It is contemplated that a single vertebral replacement device 700 can be used in isolation in a space between vertebrae. Two or more vertebral replacement devices 700 can also be positioned in a space between vertebrae without connecting systems 582, 584.

Engaging members 720, 721, 723 each include an engaging portion 730 that extends through the central chamber 614 of the disc replacement members 600, 601 and engages the adjacent upper surface 610 of disc replacement member 600 and the lower surface 612 of disc replacement member 601. Engaging portions 730 include a pair of side by side tabs 732 positionable in respective ones of the grooves 642 along upper surface 610 or grooves 646 along lower surface 612. Tabs 732 can each include a tapered upper surface 733 extending from an outer end thereof to facilitate passage of the disc replacement member 600, 601 thereover and to inwardly deflect the engaging members 720, 721, 723 as disc replacement members 600, 601 are moved therealong. When assembled, disc replacement member 600 includes lower surface 612 positioned against upper end surface 714 of vertebral body member 710. A lower engagement surface of engaging member 732 extends along the adjacent upper surface 610 along side walls 620, 622 to axially secure disc replacement member 600 to vertebral body member 710. Disc replacement member 601 is similarly secured to the lower end of vertebral body member 710.

Figure 32:
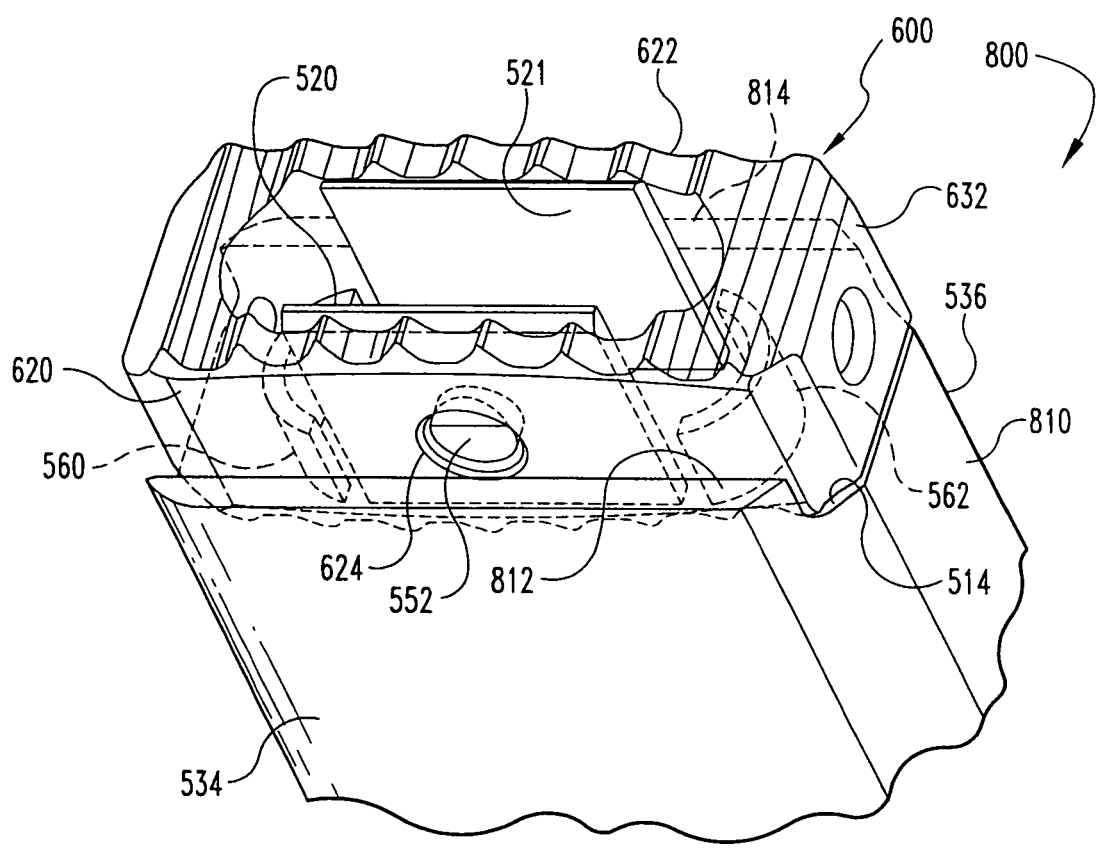
FIG. 32 is a perspective view of a portion of another embodiment vertebral replacement device.

Referring to FIG. 32, another embodiment vertebral replacement device 800 includes another embodiment vertebral body member 810 engaged to disc replacement member 600. Vertebral body member 810 can be similar to vertebral body member 510, and like elements are designated with the same reference numerals. Vertebral body member 810 includes a first flange 812 extending upwardly from upper end surface 514 along side wall 534 and a second flange 814 extending upwardly from upper end surface 514 along side wall 536. The lower end of vertebral body member 810 can similarly be provided with flanges 816, 818 (FIG. 33) along side walls 534, 536.

When stacked on vertebral body member 810, side walls 620, 622 of disc replacement member 600 are received between engaging members 520, 521 and the adjacent flange 812, 814. Flanges 812, 814 can engage or contact the outer surface of side walls 620, 622 to provide stability for the assembled vertebral replacement device 800 by resisting lateral movement and rotational movement of the disc replacement members 600, 601 relative to vertebral body member 810. The overall width between side walls 534, 536 of vertebral body member 510 can be greater than the width between side walls 620, 622 of disc replacement members 600, 601 to accommodate flanges 812, 814, 816, 818.

Figure 34:
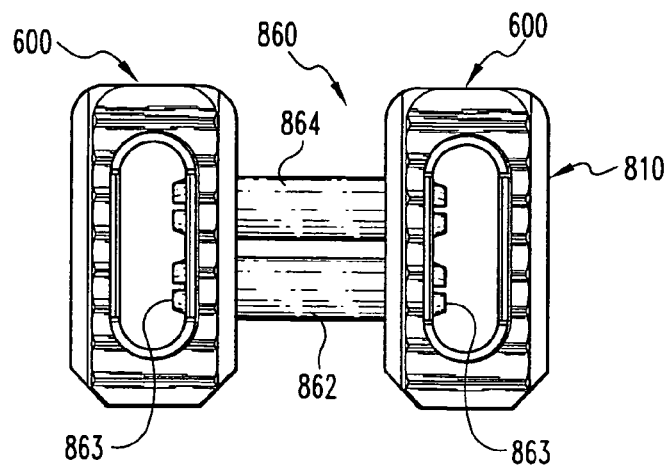
FIG. 34 is a plan view of the assembly of FIG. 33.
Figure 33:
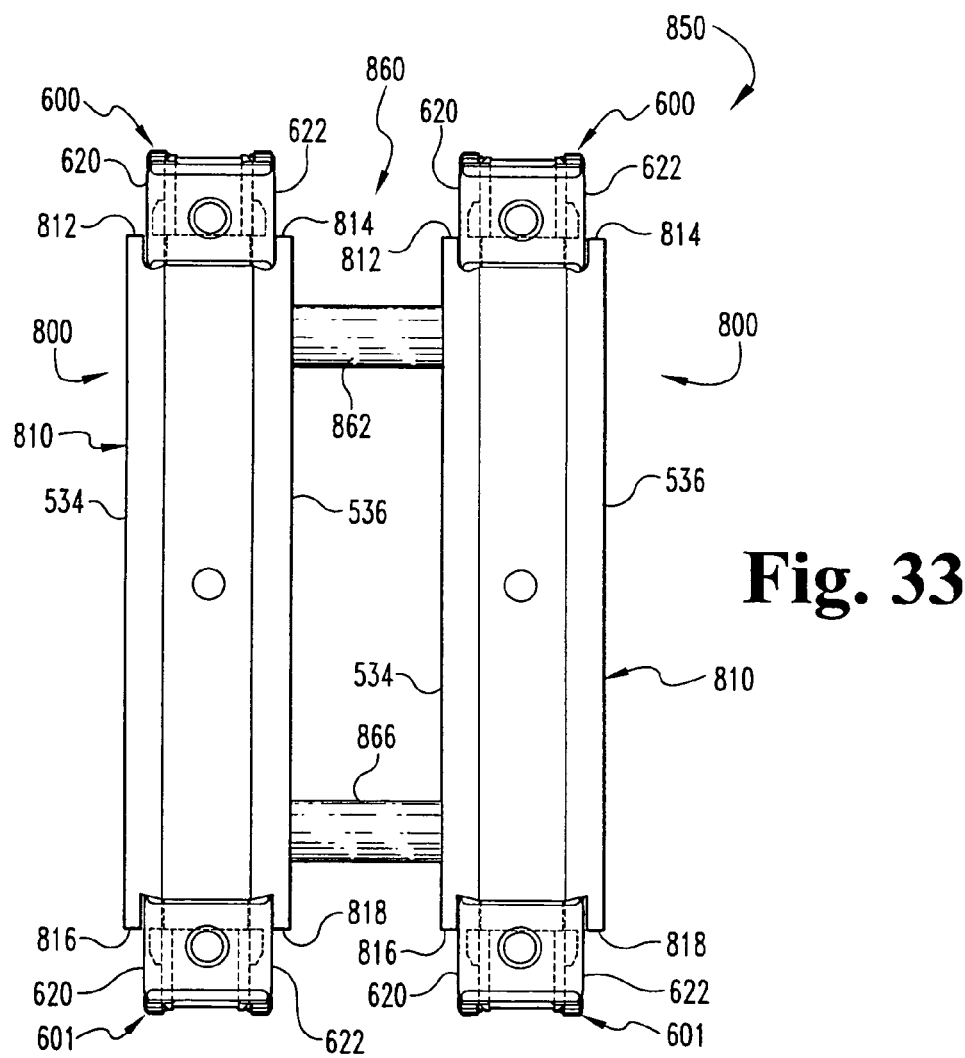
FIG. 33 is an elevation view of another embodiment assembly comprising the vertebral replacement device of FIG. 32.

Referring to FIGS. 33, 34, a pair of vertebral replacement devices 800 are connected with another embodiment connecting system 860. Connecting system 860 also has application with the other embodiment vertebral replacement devices discussed herein. Connecting system 860 includes rods 862, 864, 866 and a fourth rod (not shown) below rod 864 in FIG. 34 and behind rod 866 in FIG. 33 extending between and coupled with the adjacent medial side walls 534, 536 of the vertebral body members 810. Connecting system 860 provides stability to the pair of vertebral replacement devices to assist in maintaining devices 800 in the inserted position in a space between vertebrae. Other numbers of rods for connecting system 860 are also contemplated, including a single rod, two rods, three rods, or five or more rods.

Various coupling mechanisms at the ends of rods 862, 864, 866 are contemplated. In the illustrated embodiment, ends 863 of rod 862, for example, include a resilient collet-type end that includes a number of fingers with enlarged ends that inwardly deflect for insertion into an opening in the side walls 534, 536. With the enlarged end portions of the resilient fingers in the chamber of vertebral body member 510, the resilient fingers thereafter return toward their pre-insertion configuration to engage the corresponding side wall 534, 536. Other connections between side walls 534, 536 and rods 862, 864, 866 are also contemplated, including threaded engagement, snap fits, friction or interference fits, welded or fused connections, and combinations thereof.

Figure 35:
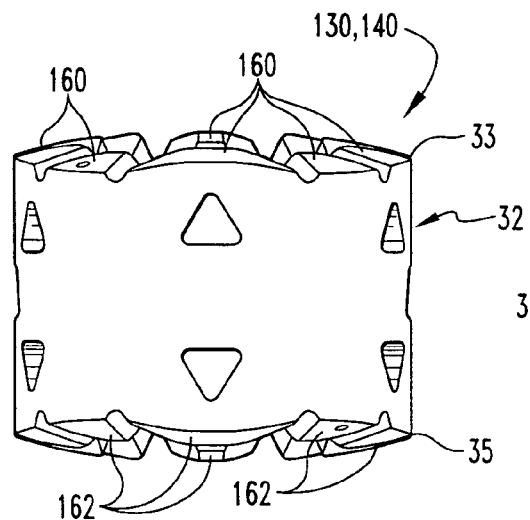
FIG. 35 is an elevation view of a disc replacement member comprising a portion of another embodiment vertebral replacement device.
Figure 36:
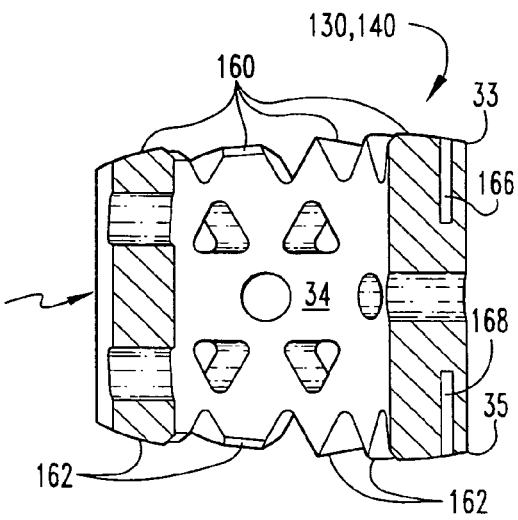
FIG. 36 is a section view through line 36-36 of FIG. 35.

FIGS. 35-36 show another embodiment for disc replacement members 130, 140 that are similar to disc replacement members 30, 40 discussed above. Accordingly, like elements are designated with like reference numerals. The disc replacement members 130, 140 include a body 32 extending between upper and lower ends 33, 35. A number of upper bearing surfaces 160 are provided about upper end 33, and a number of lower bearing surfaces 162 are provided about lower end 35. Bearing surface 160, 162 can be similar to bearing surfaces 60, 62 discussed above, but are convexly curved so that bearing surfaces 160, 162 can conform to a concave curvature of an adjacent vertebral endplate.

Figure 37:
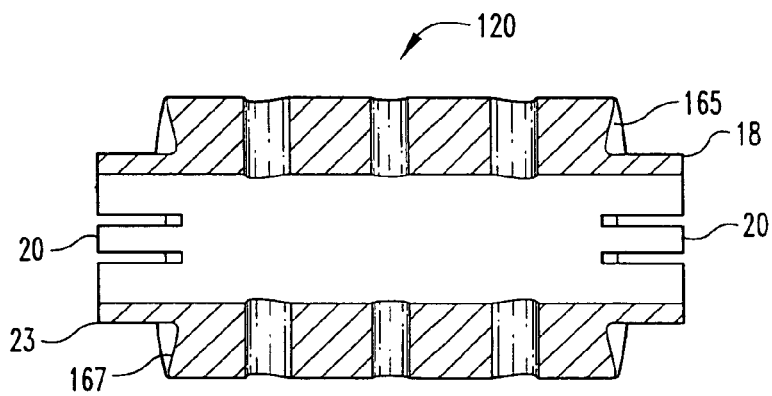
FIG. 37 is a section view along the longitudinal axis of a vertebral body member engageable to the disc replacement member of FIG. 35.
Figure 38:
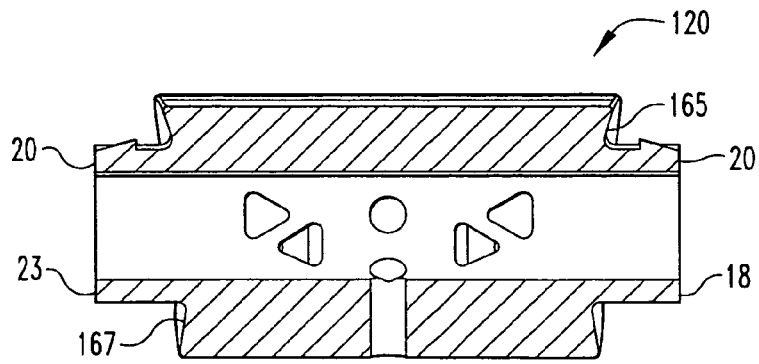
FIG. 38 is another section view of the vertebral body member of FIG. 37 rotated 90 degrees about the longitudinal axis.

Body 32 can also be provided with an upper radiographic marker 166 and a lower radiographic marker 168 to facilitate visualization of members 130, 140 in the patients body should body 32 be comprised of radiolucent material. Furthermore, upper surfaces 160 and lower surfaces 162 can be tapered so that one side of body 32 has a height greater than the other, conforming disc replacement members 130, 140 to a desired angulation between the vertebral endplates Section views of vertebral body member 120 are shown in FIGS. 37, 38. Vertebral body member 120 can be identical to vertebral body member 12 discussed above, except that vertebral body member 120 can be for engagement with upper and lower disc replacement members 130, 140. Vertebral body member 120 is attachable to upper and lower disc replacement members 130, 140 to form a vertebral replacement device. Vertebral body member 120 includes an upper end surface 165 against which lower bearing surfaces 162 of upper disc replacement member 130 are positioned. An upper extension 18 and engaging member 20 facilitate axial engagement of the upper disc replacement member 130 thereto. Vertebral body member 120 further includes a lower end surface 167 against which upper bearing surfaces 160 of lower disc replacement member 140 are positioned. A lower extension 23 and engaging member 20 facilitate axial engagement of the lower disc replacement member 140 thereto.

End surfaces 165, 167 each include a concavely curved profile that matches the convexly curved profile formed by bearing surfaces 160, 162 so that each of the bearing surfaces 160, 162 are substantially supported by a respect one of the end surfaces 165, 167 when upper and lower disc replacement members 130, 140 are secured to vertebral body member 120.

While the invention has been illustrated and described in detail in the drawings and foregoing description, the same is to be considered as illustrative and not restrictive in character. All changes and modifications that come within the spirit of the invention are desired to be protected.

What is claimed is:

1. A device positionable in a spinal column between endplates of first and second vertebrae, comprising:
   a first member including a body extending from a first end surface for engaging an endplate of the first vertebra to an opposite second end surface, said body of said first member extending around at least one chamber and said at least one chamber opens at said first and second end surfaces, said at least one chamber comprising a middle chamber and a pair of end chambers on opposite sides of said middle chamber, each of said end chambers being separated from said middle chamber by a wall; and
   a second member including a body extending along a longitudinal axis between a first end surface and an opposite second end surface, said second end surface of said first member positioned in contact with said first end surface of said second member, wherein said second member includes at least one engaging member extending along said longitudinal axis away from said first end surface of said second member and at least two extensions extending along said longitudinal axis away from said first end surface of said second member, each of said at least two extensions being parallel relative to one another and being equidistant from said at least one engaging member, said at least two extensions comprising a first extension positioned in one of said pair of end chambers and a second extension positioned in the other of said pair of end chambers, said at least two extensions contacting said body of said first member at opposite sides of said body to resist rotation of said first member relative to said second member about said longitudinal axis and said at least one engaging member being positioned in said middle chamber and in contact with said body of said first member to resist displacement of said first member away from said second member along said longitudinal axis.

2. The device of claim 1, wherein said first end surface of said body of said second member is smooth and said second end surface of said body of said first member includes a plurality of anti-expulsion features defined by a plurality of recesses extending across said second end surface of said first member, said anti-expulsion features being positioned in contact with said smooth first end surface of said second member and said plurality of recesses forming avenues for bone growth between said first member and said second member.

3. The device of claim 2, wherein said first end surface of said second member is concavely curved and said anti-expulsion features of said first member define a convex curvature adapted to bear against said concavely curved first end surface of said second member.

4. The device of claim 1, wherein said end chambers define opposite curved ends that define opposite concavely curved portions of said at least one chamber.

5. The device of claim 1, wherein said at least one engaging member includes a protrusion projecting laterally outwardly therefrom, said protrusion engaging an opening in said body of said first member.

6. The device of claim 1, wherein said first member and said second member each define a cross-section orthogonally to said longitudinal axis that includes a convexly curved outer surface portion and an opposite concavely outer surface portion, said outer surface portions being connected by opposite convexly curved outer surface end portions.

7. The device of claim 1, wherein said device comprises a third member including a body extending from a first end surface for engaging an endplate of the second vertebra to an opposite second end surface positioned in contact with said second end surface of said second member, said body of said third member extending around at least one second chamber and said at least one second chamber opens at least at said second end surface of said third member, said at least one second chamber comprising a middle chamber and a pair of end chambers on opposite sides of said middle chamber, each of said end chambers being separated from said middle chamber by a wall, wherein said second member includes at least one second engaging member extending along said longitudinal axis away from said second end surface of said second member and at least two second extensions extending along said longitudinal axis away from said second end surface of said second member, each of said at least two second extensions being parallel relative to one another and being equidistant from said at least one second engaging member, said at least two second extensions comprising a third extension positioned in one of said pair of end chambers in said third member and a fourth extension positioned in the other of said pair of end chambers in said third member, said at least two second extensions contacting said body of said third member at opposite sides of said body to resist rotation of said third member relative to said second member about said longitudinal axis and said at least one second engaging member being positioned in said middle chamber of said third member and in contact with said body of said third member to resist displacement of said third member away from said second member along said longitudinal axis.

* * * * *